United States Patent
Hammock et al.

(10) Patent No.: US 11,572,347 B2
(45) Date of Patent: Feb. 7, 2023

(54) ORALLY AVAILABLE SEH/PDE4 DUAL INHIBITORS

(71) Applicants: THE REGENTS OF THE UNIVERSITY OF CALIFORNIA, Oakland, CA (US); GOETHE-UNIVERSITY FRANKFURT, Frankfurt am Main (DE)

(72) Inventors: Bruce D. Hammock, Davis, CA (US); Rene Bloecher, Davis, CA (US); Christophe Morisseau, Davis, CA (US); Yang Kevin Xiang, Davis, CA (US); Karen Wagner, Davis, CA (US); Todd Harris, Davis, CA (US); Raghavender Reddy Gopireddy, Davis, CA (US); Eugen Proschak, Frankfurt (DE)

(73) Assignees: The Regents of the University of California, Oakland, CA (US); Goethe-University Frankfurt, Frankfurt (DE)

( * ) Notice: Subject to any disclaimer, the term of this patent is extended or adjusted under 35 U.S.C. 154(b) by 0 days.

(21) Appl. No.: 16/755,861

(22) PCT Filed: Oct. 18, 2018

(86) PCT No.: PCT/US2018/056532
§ 371 (c)(1),
(2) Date: Apr. 13, 2020

(87) PCT Pub. No.: WO2019/079609
PCT Pub. Date: Apr. 25, 2019

(65) Prior Publication Data
US 2021/0395202 A1    Dec. 23, 2021

Related U.S. Application Data

(60) Provisional application No. 62/574,908, filed on Oct. 20, 2017.

(51) Int. Cl.
| | | |
|---|---|---|
| C07D 211/62 | (2006.01) | |
| C07C 235/46 | (2006.01) | |
| C07C 235/48 | (2006.01) | |
| C07D 209/34 | (2006.01) | |

(52) U.S. Cl.
CPC .......... *C07D 211/62* (2013.01); *C07C 235/46* (2013.01); *C07C 235/48* (2013.01); *C07D 209/34* (2013.01)

(58) Field of Classification Search
CPC ................ C07D 211/62; C07D 209/34; C07C 209/34; C07C 235/46; C07C 235/18
See application file for complete search history.

(56) References Cited

U.S. PATENT DOCUMENTS

2012/0028969 A1   2/2012  Barnes et al.
2020/0087258 A1*  3/2020  Zahn ................... A61K 31/453

FOREIGN PATENT DOCUMENTS

WO    2007/043653   *  4/2007
WO    2009/073772   *  6/2009

OTHER PUBLICATIONS

Blochner, J Med CHem, 2016, vol. 59, pp. 61-81. (Year: 2016).*
Bai, BMJ. Science Daily, Oct. 28, 2019, pp. 1-3. (Year: 2019).*
Pubchem, Summary for CID 4647308, N-[(4-Fluorophenyl)methyl] cyclohexanecarboxamide, Sep. 16, 2005, pp. 1-13.
International Search Report for PCT/US2018/056532 dated Jan. 23, 2019, 4 pages.
Written Opinion of the International Searching Authority for PCT/US2018/056532 dated Jan. 23, 2019, 5 pages.

* cited by examiner

*Primary Examiner* — D Margaret M Seaman
(74) *Attorney, Agent, or Firm* — Mintz, Levin, Cohn, Ferris, Glovsky and Popeo, P.C.

(57) ABSTRACT

Provided herein are novel bioavailable dual inhibitors capable of inhibiting both soluble epoxide hydrolase (sEH) and phosphodiesterase 4 (PDE4), and methods of using the same.

25 Claims, 8 Drawing Sheets

ORALLY AVAILABLE SEH/PDE4 DUAL INHIBITORS

CROSS-REFERENCES TO RELATED APPLICATIONS

This application claims priority to U.S. Provisional Application No. 62/574,908, filed Oct. 20, 2017, which is incorporated herein in its entirety for all purposes.

STATEMENT AS TO RIGHTS TO INVENTIONS MADE UNDER FEDERALLY SPONSORED RESEARCH AND DEVELOPMENT

This invention was made with government support under Grant Nos. DC008072, ES002710, ES004699, ES007059, and HL086350, awarded by the National Institutes of Health. The government has certain rights in the invention.

BACKGROUND OF THE INVENTION

Multi-target ligands are designed to improve efficacy and safety in treatment of complex diseases [Ref. 2]. Target combinations are selected to generate a synergistic effect on one or several physiological disorders. In a previous study, a synergistic analgesic effect of soluble epoxide hydrolase (sEH) inhibitors and phosphodiesterase 4 (PDE4) inhibitors were discovered as reported [Ref. 1]. To develop sEH/PDE4 dual inhibitors, the polypharmacological agents require the combination of at least two pharmacophores in one molecule.

Located in the arachidonic acid cascade, cytochrome P450 (CYP450) forms several epoxy-fatty acids such as epoxyeicosatrienoic acids (EETs), which are metabolized by the sEH to their corresponding diols, called dihydroxy eicosatrienoic acid (DHETs) [Ref. 6]. Inhibition of sEH elevates EET levels causing beneficial physiological effects in animal models of inflammation [Ref. 7], pain [Ref. 8], hypertension [Ref. 6] and depression [Ref. 9]. PDE4 is the major enzyme degrading cAMP into 5-AMP and PDE4 inhibition increases cAMP levels, leading to a down-regulation of multiple inflammatory mediators [Ref. 10]. PDE4 is therefore a valuable target in the treatment of inflammatory diseases such as psoriasis, psoriatic arthritis (PsA) [Ref. 10], chronic obstructive pulmonary diseases (COPD) [Ref. 11] and asthma [Ref. 12]. Additionally, cAMP levels in neurons are shown to be correlated with symptoms of neuronal disorders such as depression [Ref. 13], schizophrenia [Ref. 14] and Alzheimer's disease [Ref. 15].

Nevertheless, the historical challenge of PDE4 based therapy is the limited therapeutic index, caused by side effects such as nausea or vasculitis [Ref. 11]. The multi-target ligand approach has potential for an improvement in this challenge.

Described herein, inter alia, are solutions to these and other problems in the art.

BRIEF SUMMARY OF THE INVENTION

In one aspect, the present invention provides a compound of formula I:

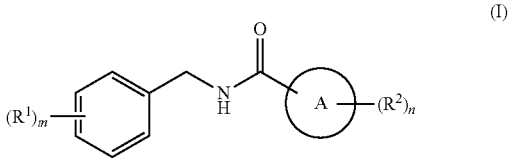

or a pharmaceutically acceptable salt thereof,
wherein:
each $R^1$ is independently hydrogen, halogen, $C_1$-$C_6$ alkyl, $C_1$-$C_6$ haloalkyl, $C_1$-$C_6$ alkoxy, or $C_1$-$C_6$ haloalkoxy, provided that at least one $R^1$ is not hydrogen;
ring A is $C_3$-$C_8$ cycloalkyl, 3-8 membered heterocycloalkyl, $C_6$-$C_{12}$ aryl, or 5-12 membered heteroaryl, wherein the 3-8 membered heterocycloalkyl and the 5-12 membered heteroaryl have 1-4 heteroatoms selected from N, O, and S;
each $R^2$ is independently hydrogen, halogen, $C_1$-$C_6$ alkyl, $C_1$-$C_6$ haloalkyl, —C(O)NR³R⁴, —NR³C(O)R⁵, —C(O)OR⁵, —OC(O)R⁵, —C(O)R⁵, —SO₂NR³R⁴, —NR³SO₂R⁵, —SO₂R⁵, —NR³R⁴, or —OR⁵; or two adjacent $R^2$ groups are combined to form a 3-6 membered heterocycle having 1-2 heteroatoms selected from N, O, and S, which is optionally substituted with oxo;
$R^3$, $R^4$, and $R^5$ are each independently hydrogen, $C_1$-$C_6$ alkyl, $C_1$-$C_6$ haloalkyl, or $C_3$-$C_8$ cycloalkyl;
subscript m is an integer from 1 to 5; and
subscript n is an integer from 1 to 4.

In a second aspect, the present invention provides a pharmaceutical composition including the compound of formula I and one or more pharmaceutically acceptable excipients.

In a third aspect, the present invention provides a method of inhibiting soluble epoxide hydrolase (sEH) and phosphodiesterase 4 (PDE4). The method includes contacting the soluble epoxide hydrolase (sEH) and phosphodiesterase 4 (PDE4) with an effective amount of the compound of formula I, or the pharmaceutical composition including the compound of formula I, thereby inhibiting the soluble epoxide hydrolase (sEH) and phosphodiesterase 4 (PDE4).

In a fourth aspect, the present invention provides a method of treating an inflammatory disease. The method includes administering to a subject in need thereof a therapeutically effective amount of the compound of formula I, or the pharmaceutical composition including the compound of formula I, thereby treating the inflammatory disease.

BRIEF DESCRIPTION OF THE DRAWINGS

FIG. 2A shows the maximal increases in PM-AKAR3 FRET ratio after stimulation with various novel compounds (1p M) or with PDE4 inhibitor Rolipram (1p M); FIG. 2B shows normalized percentile maximal FRET responses of PM-AKAR3 biosensor against the increases induced by treatment with novel compounds and Rolipram, respectively;

and FIG. 2C shows normalized novel compound induced dose response curves of PM-AKAR3 biosensor (IC50, Compound 1 at 1.9±0.03 nM, Compound 19 at 128±0.05 nM, Compound 20 at 3.9±0.06 nM, Compound 23/RBH61 at 8.1±0.05 nM) and compared with Rolipram (IC50, 340±0.06 nM) respectively.

DETAILED DESCRIPTION

I. General

Figure 1:
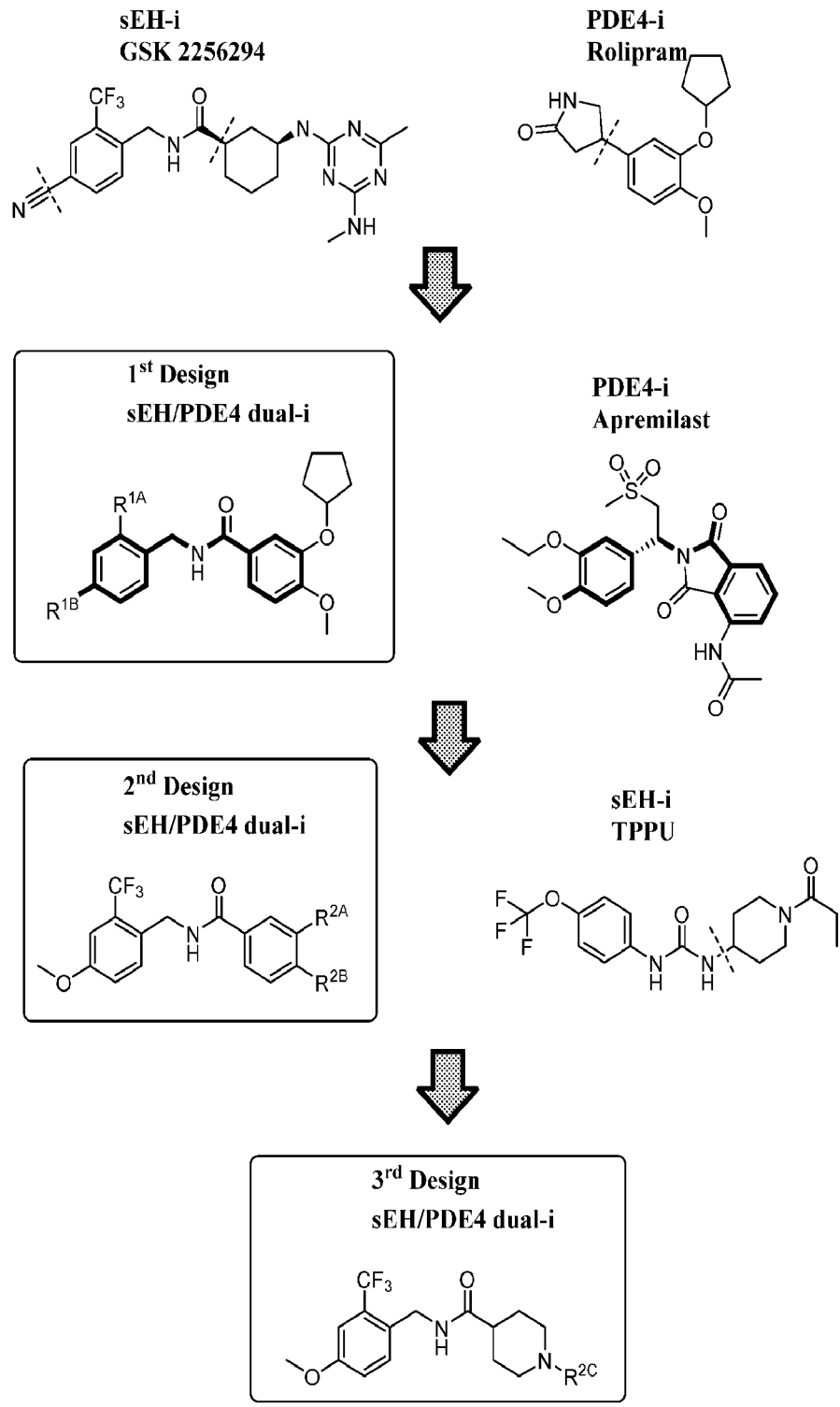
FIG. 1 shows the scheme of dual drug design and structural development.

The present invention provides novel compounds of formula I as sEH/PDE4 dual inhibitors. These compounds are highly potent dual ligands with $IC_{50}$ values ranging from subnano to submicromolar concentrations. Further pharmacokinetic studies of several selected compounds have led to the identification of a bioavailable dual inhibitor (RBH61).

The present invention provides a method of using compounds of formula I for treatment of an inflammatory disease.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as $C_1$-$C_2$, $C_1$-$C_3$, $C_1$-$C_4$, $C_1$-$C_5$, $C_1$-$C_6$, $C_1$-$C_7$, $C_1$-$C_8$, $C_1$-$C_9$, $C_1$-$C_{10}$, $C_2$-$C_3$, $C_2$-$C_4$, $C_2$-$C_5$, $C_2$-$C_6$, $C_3$-$C_4$, $C_3$-$C_5$, $C_3$-$C_6$, $C_4$-$C_5$, $C_4$-$C_6$ and $C_5$-$C_6$. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_3$-$C_6$, $C_4$-$C_6$, $C_5$-$C_6$, $C_3$-$C_8$, $C_4$-$C_8$, $C_5$-$C_8$, $C_6$-$C_8$, $C_3$-$C_9$, $C_3$-$C_{10}$, $C_3$-$C_{11}$, and $C_3$-$C_{12}$. Saturated monocyclic cycloalkyl rings include, for example, cyclopropyl, cyclobutyl, cyclopentyl, cyclohexyl, and cyclooctyl.

Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. Cycloalkyl groups can be substituted or unsubstituted.

"Alkoxy" refers to an alkyl group having an oxygen atom that connects the alkyl group to the point of attachment: alkyl-O—. As for the alkyl group, alkoxy groups can have any suitable number of carbon atoms, such as $C_1$-$C_6$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Halogen" refers to fluorine, chlorine, bromine and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_1$-$C_6$. For example, haloalkyl includes trifluoromethyl, fluoromethyl, etc. In some embodiments, the term "perfluoro" can be used to define a compound or radical where all the hydrogens are replaced with fluorine. For example, perfluoromethane includes 1,1,1-trifluoromethyl.

"Heterocycloalkyl" refers to a saturated ring system having from 3 to 12 ring members and from 1 to 4 heteroatoms of N, O and S. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. The heteroatoms can also be oxidized, such as, but not limited to, —S(O)— and —S(O)$_2$—. Heteroaryl groups can include any number of ring atoms, such as, 5 to 6, 5 to 8, 6 to 8, 5 to 9, 5 to 10, 5 to 11, or 5 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Isomers" refers to compounds with the same chemical formula but which are structurally distinguishable. Certain compounds of the present invention possess asymmetric carbon atoms (optical centers) or double bonds; the racemates, diastereomers, geometric isomers and individual isomers are all intended to be encompassed within the scope of the present invention.

"Tautomer" refers to one of two or more structural isomers which exist in equilibrium and which are readily converted from one form to another.

The present invention includes all tautomers and stereoisomers of compounds of the present invention, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject in need thereof" refers to a living organism suffering from or prone to a condition that can be treated by administration of a pharmaceutical composition as provided herein. Non-limiting examples include humans, other mammals, for example primates cows, sheep, goats, horses, dogs, cats, rabbits, rats, mice and the like, and other non-mammalian animals.

"Inhibition", "inhibits" and "inhibitor" refer to a compound that prohibits or a method of prohibiting, a specific action or function.

"Soluble epoxide hydrolase (sEH) inhibitor" refers to a compound that prohibits the function of sEH, which metabolizes epoxy-fatty acids such as epoxyeicosatrienoic acids (EETs) to their corresponding diols, called dihydroxy eicosatrienoic acid (DHETs). Inhibition of sEH elevates EET levels.

"Phosphodiesterase 4 (PDE4) inhibitor" refers to a compound that prohibits the function of PDE4, which is the major enzyme degrading cAMP into 5-AMP. PDE4 inhibition increases cAMP levels.

"sEH/PDE4 dual inhibitor" refers to a compound that prohibits the function of both sEH and PDE4.

"Disorder" or "condition" refers to a state of being or health status of a patient or subject capable of being treated with the sEH/PDE4 dual inhibitors of the present invention.

Examples of disorders or conditions include, but are not limited to, inflammatory diseases such as inflammation, pain, hypertension, depression, psoriasis, psoriatic arthritis, chronic obstructive pulmonary disease (COPD), or asthma; or neuronal disorders such as depression, schizophrenia, and Alzheimer's disease.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

In this disclosure, "comprises," "comprising," "containing" and "having" and the like can have the meaning ascribed to them in U.S. Patent law and can mean "includes," "including," and the like.

"A," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substitutent group, the compound is substituted with at least one substituent group, wherein each substitutent group is optionally different.

Abbreviations: % of Bl—percent of baseline; $^{13}$C NMR—Carbon nuclear magnetic resonance; $^1$H NMR—Proton nuclear magnetic resonance; 5-AMP—5 adenosine monophosphate; cAMP—cyclic adenosine monophosphate; $C_{max}$— the maximum (or peak) serum concentration that a drug achieves in a specified compartment; COPD—chronic obstructive pulmonary diseases; Ctrl—control; CYP450—cytochrome P450; DHETs—dihydroxy eicosatrienoic acid; DMSO—Dimethylsulfoxide; dual-1—dual inhibitor; EETs—epoxyeicosatrienoic acids; ESI—Electrospray ionization; FBS—Fetal bovine serum; FDA—Food and Drug Administration; FRET—Forster Resonance Energy Transfer; GSK—Glaxosmithkline; HPLC—High-performance liquid chromatography; HRMS—High-resolution mass spectrometry; hsEH—human soluble epoxide hydrolase; $IC_{50}$— the concentration of an inhibitor where the response (or binding) is reduced by halft LPS—lipopolysaccharide; mg/kg—mg compound per kg bodyweight; PD—pharmacodynamics; PDE4—phosphodiesterase 4; PDE4-1-phosphodiesterase 4 inhibitor; PEG300—Polyethylene Glycol 300; PK—pharmacokinetic; PKA—protein kinase A; PO—per oral; PsA—psoriatic arthritis; rsEH—rat soluble epoxide hydrolase; rt—room temperature; sEH—soluble epoxide hydrolase; sEH-1-soluble epoxide hydrolase inhibitor; $T_{max}$—the amount of time that a drug is present at the maximum concentration in plasma; TWL—Thermal withdrawal threshold; ws—water solubility III. Compounds The present invention provides compounds of formula I. In some embodiments, the present invention provides a compound of formula I:

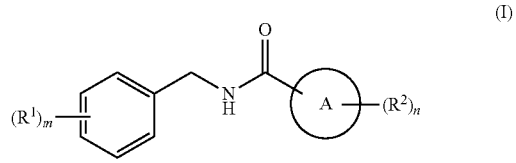

or a pharmaceutically acceptable salt thereof,
wherein:

each $R^1$ is independently hydrogen, halogen, $C_1$-$C_6$ alkyl, $C_1$-$C_6$ haloalkyl, $C_1$-$C_6$ alkoxy, or $C_1$-$C_6$ haloalkoxy, provided that at least one $R^1$ is not hydrogen;

ring A is $C_3$-$C_8$ cycloalkyl, 3-8 membered heterocycloalkyl, $C_6$-$C_{12}$ aryl, or 5-12 membered heteroaryl, wherein the 3-8 membered heterocycloalkyl and the 5-12 membered heteroaryl have 1-4 heteroatoms selected from N, O, and S;

each $R^2$ is independently hydrogen, halogen, $C_1$-$C_6$ alkyl, $C_1$-$C_6$ haloalkyl, —C(O)NR$^3$R$^4$, —NR$^3$C(O)R$^5$, —C(O)OR$^5$, —OC(O)R$^5$, —C(O)R$^5$, —SO$_2$NR$^3$R$^4$, —NR$^3$SO$_2$R$^5$, —SO$_2$R$^5$, —NR$^3$R$^4$, or —OR$^5$; or two adjacent $R^2$ groups are combined to form a 3-6 membered heterocycle having 1-2 heteroatoms selected from N, O, and S, which is optionally substituted with oxo;

$R^3$, $R^4$, and $R^5$ are each independently hydrogen, $C_1$-$C_6$ alkyl, $C_1$-$C_6$ haloalkyl, or $C_3$-$C_8$ cycloalkyl;

subscript m is an integer from 1 to 5; and subscript n is an integer from 1 to 4.

In some embodiments, each $R^1$ is independently hydrogen, halogen, $C_1$-$C_6$ alkyl, $C_1$-$C_6$ haloalkyl, $C_1$-$C_6$ alkoxy, or $C_1$-$C_6$ haloalkoxy, provided that at least one $R^1$ is not hydrogen. In some embodiments, each $R^1$ is independently hydrogen, halogen, $C_1$-$C_4$ alkyl, $C_1$-$C_4$ haloalkyl, $C_1$-$C_4$ alkoxy, or $C_1$-$C_4$ haloalkoxy, provided that at least one $R^1$ is not hydrogen. In some embodiments, each $R^1$ is independently hydrogen, $C_1$-$C_4$ alkyl, $C_1$-$C_4$ haloalkyl, $C_1$-$C_4$ alkoxy, or $C_1$-$C_4$ haloalkoxy, provided that at least one $R^1$ is not hydrogen. In some embodiments, each $R^1$ is independently $C_1$-$C_4$ alkyl, $C_1$-$C_4$ haloalkyl, $C_1$-$C_4$ alkoxy, or $C_1$-$C_4$ haloalkoxy. The $C_1$-$C_4$ alkyl of $R^1$ can be methyl, ethyl, propyl, isopropyl, butyl, isobutyl, sec-butyl, or tert-butyl. The $C_1$-$C_4$ haloalkyl of $R^1$ can be trifluoromethyl, fluoromethyl, 2,2,2-trifluoroethyl. The $C_1$-$C_4$ alkoxy of $R^1$ can be methoxy, ethoxy, propoxy, iso-propoxy, butoxy, 2-butoxy, iso-butoxy, sec-butoxy, or tert-butoxy. The $C_1$-$C_4$ haloalkoxy of $R^1$ can be trifluoromethoxy, 2,2,2-trifluoroethoxy, or perfluoroethoxy. In some embodiments, at least one $R^1$ is —CH$_3$. In some embodiments, at least one $R^1$ is —CF$_3$. In some embodiments, at least one $R^1$ is —OCH$_3$. In some embodiments, each $R^1$ is independently hydrogen, —CH$_3$, —OCH$_3$, or —CF$_3$, provided that at least one $R^1$ is not hydrogen. In some embodiments, each $R^1$ is independently-OCH$_3$ or —CF$_3$.

In some embodiments, subscript m is an integer from 1 to 4. In some embodiments, subscript m is an integer from 1 to 3. In some embodiments, subscript m is an integer from 1 to 2. In some embodiments, subscript m is 2.

In some embodiments, the compound of formula I is a compound of formula I-1:

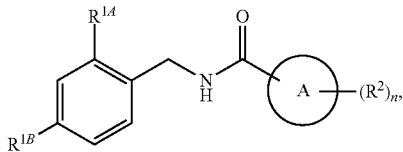

wherein $R^{1A}$ and $R^{1B}$ are each independently hydrogen, halogen, $C_1$-$C_6$ alkyl, $C_1$-$C_6$ haloalkyl, $C_1$-$C_6$ alkoxy, or $C_1$-$C_6$ haloalkoxy, provided that $R^{1A}$ and $R^{1B}$ are not both hydrogen; and ring A, $R^2$, and subscript n are as defined and described herein.

In some embodiments, $R^{1A}$ and $R^{1B}$ are each independently hydrogen, halogen, $C_1$-$C_6$ alkyl, $C_1$-$C_6$ haloalkyl, $C_1$-$C_6$ alkoxy, or $C_1$-$C_6$ haloalkoxy, provided that $R^{1A}$ and $R^{1B}$ are not both hydrogen. In some embodiments, $R^{1A}$ and $R^{1B}$ are each independently hydrogen, halogen, $C_1$-$C_4$ alkyl, $C_1$-$C_4$ haloalkyl, $C_1$-$C_4$ alkoxy, or $C_1$-$C_4$ haloalkoxy, provided that $R^{1A}$ and $R^{1B}$ are not both hydrogen. In some embodiments, $R^{1A}$ and $R^{1B}$ are each independently $C_1$-$C_4$ haloalkyl, or $C_1$-$C_4$ alkoxy. The $C_1$-$C_4$ alkyl of $R^{1A}$ or $R^{1B}$ can be methyl, ethyl, propyl, isopropyl, butyl, isobutyl, sec-butyl, or tert-butyl. The $C_1$-$C_4$ haloalkyl of $R^{1A}$ or $R^{1B}$ can be trifluoromethyl, fluoromethyl, 2,2,2-trifluoroethyl. The $C_1$-$C_4$ alkoxy of $R^{1A}$ or $R^{1B}$ can be methoxy, ethoxy, propoxy, iso-propoxy, butoxy, 2-butoxy, iso-butoxy, sec-butoxy, or tert-butoxy. The $C_1$-$C_4$ haloalkoxy of $R^{1A}$ and $R^{1B}$ can be trifluoromethoxy, 2,2,2-trifluoroethoxy, or perfluoroethoxy.

In some embodiments, $R^{1A}$ and $R^{1B}$ are each independently H, —$CH_3$, —$CF_3$, or —$OCH_3$, provided that $R^{1A}$ and $R^{1B}$ are not both hydrogen. In some embodiments, $R^{1A}$ and $R^{1B}$ are each independently —$CF_3$ or —$OCH_3$. In some embodiments, $R^{1A}$ is —$CF_3$. In some embodiments, $R^{1A}$ is —$OCH_3$. In some embodiments, $R^{1B}$ is —$CF_3$. In some embodiments, $R^{1B}$ is —$OCH_3$. In some embodiments, $R^{1A}$ is —$CH_3$ and $R^{1B}$ is H. In some embodiments, $R^{1A}$ is —$CF_3$ and $R^{1B}$ is H. In some embodiments, $R^{1A}$ is —$CF_3$ and $R^{1B}$ is —$OCH_3$.

In some embodiments, the compound of formula I is a compound of formula I-2:

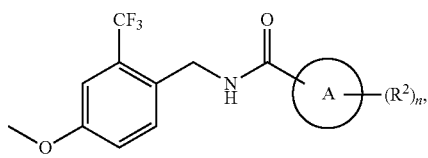

wherein ring A, $R^2$, and subscript n are as defined and described herein.

In some embodiments, ring A is $C_6$-$C_{12}$ aryl or 3-8 membered heterocycloalkyl having 1-4 heteroatoms of N, O, and S. In some embodiments, ring A is $C_6$-$C_{12}$ aryl. The $C_6$-$C_{12}$ aryl of ring A can be phenyl, naphthyl, or biphenyl. In some embodiments, ring A is phenyl. In some embodiments, ring A is 3-8 membered heterocycloalkyl having 1-4 heteroatoms of N, O, and S. In some embodiments, ring A is 3-8 membered heterocycloalkyl having at least one nitrogen atom. The 3-8 membered heterocycloalkyl of ring A can be pyrrolidinyl or piperidinyl. In some embodiments, ring A is piperidinyl.

In some embodiments, each $R^2$ is independently hydrogen, halogen, $C_1$-$C_6$ alkyl, $C_1$-$C_6$ haloalkyl, —C(O)NR$^3$R$^4$, —NR$^3$C(O)R$^5$, —C(O)OR$^5$, —OC(O)R$^5$, —C(O)R$^5$, —$SO_2$NR$^3$R$^4$, —NR$^3$$SO_2$R$^5$, —$SO_2$R$^5$, —NR$^3$R$^4$, or —OR$^5$; and $R^3$, $R^4$, and $R^5$ are each independently hydrogen, $C_1$-$C_6$ alkyl, $C_1$-$C_6$ haloalkyl, or $C_3$-$C_8$ cycloalkyl. In some embodiments, each $R^2$ is independently hydrogen, halogen, $C_1$-$C_6$ alkyl, $C_1$-$C_6$ haloalkyl, —NHC(O)R$^5$, or —OR$^5$; and $R^5$ is hydrogen, $C_1$-$C_6$ alkyl, $C_1$-$C_6$ haloalkyl, or $C_3$-$C_8$ cycloalkyl. In some embodiments, each $R^2$ is independently hydrogen, halogen, $C_1$-$C_6$ alkyl, $C_1$-$C_6$ haloalkyl, —NHC(O)—$C_1$-$C_6$ alkyl, —O—$C_1$-$C_6$ alkyl, —O—$C_1$-$C_6$ haloalkyl, or —O—$C_3$-$C_8$ cycloalkyl. In some embodiments, each $R^2$ is independently hydrogen, halogen, $C_1$-$C_4$ alkyl, $C_1$-$C_4$ haloalkyl, —NHC(O)—$C_1$-$C_4$ alkyl, —O—$C_1$-$C_4$ alkyl, —O—$C_1$-$C_4$ haloalkyl, or —O—$C_3$-$C_6$ cycloalkyl. The halogen of $R^2$ can be F, Cl, Br, or I. The $C_1$-$C_4$ alkyl of $R^2$, alone or as a part of another group, can be methyl, ethyl, propyl, isopropyl, butyl, isobutyl, sec-butyl, or tert-butyl. The $C_1$-$C_4$ haloalkyl of $R^2$, alone or as a part of another group, can be difluoromethyl, trifluoromethyl, fluoromethyl, 2,2,2-trifluoroethyl. The —O—$C_3$-$C_6$ cycloalkyl of $R^2$ can be —O— cyclopropyl, —O-cyclobutyl, —O-cyclopentyl, or —O-cyclohexyl. In some embodiments, each $R^2$ is independently H, F, Me, —$CF_3$, —NHC(O)Me, —NHC(O)Et, —OMe, —$OCHF_2$, —$OCF_3$, or —O-cyclopentyl. In some embodiments, each $R^2$ is independently H, F, Me, —NHC(O)Me, —NHC(O)Et, —OMe, —$OCHF_2$, or —O-cyclopentyl. In some embodiments, each $R^2$ is independently H, F, —OMe, or —O-cyclopentyl. In some embodiments, at least one $R^2$ is —O— cyclopentyl.

In some embodiments, two adjacent $R^2$ groups are combined to form a 3-6 membered heterocycle having 1-2 heteroatoms selected from N, O, and S, which is optionally substituted with oxo. In some embodiments, two adjacent $R^2$ groups are combined to form a 3-6 membered heterocycle having at least one nitrogen atom, which is optionally substituted with oxo. In some embodiments, two adjacent $R^2$ groups are combined to form azetidine, pyrrolidine, piperidine, azetidin-2-one, pyrrolidin-2-one, or piperidin-2-one. In some embodiments, two adjacent $R^2$ groups are combined to form pyrrolidin-2-one.

In some embodiments, subscript n is an integer from 1 to 3. In some embodiments, subscript n is an integer from 1 to 2. In some embodiments, subscript n is 2. In some embodiments, subscript n is 1.

In some embodiments, ring A is phenyl. In some embodiments, the compound of formula I is a compound of formula I-3:

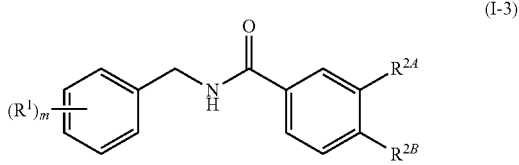

wherein:
$R^{2A}$ and $R^{2B}$ are each independently hydrogen, halogen, $C_1$-$C_6$ alkyl, $C_1$-$C_6$ haloalkyl, —C(O)NR$^3$R$^4$, —NR$^3$C(O)R$^5$, —C(O)OR$^5$, —OC(O)R$^5$, —C(O)R$^5$, —$SO_2$NR$^3$R$^4$, —NR$^3$$SO_2$R$^5$, —$SO_2$R$^5$, —NR$^3$R$^4$, or —OR⁵; or R²ᴬ and R²ᴮ together form a 3-6 membered heterocycle having 1-2 heteroatoms selected from N, O, and S;

R³, R⁴, and R⁵ are each independently hydrogen, C₁-C₆ alkyl, C₁-C₆ haloalkyl, or C₃-C₈ cycloalkyl; and R¹ and subscript m are as defined and described herein.

In some embodiments, R²ᴬ and R²ᴮ are each independently hydrogen, halogen, C₁-C₆ alkyl, C₁-C₆ haloalkyl, —C(O)NR³R⁴, —NR³C(O)R⁵, —C(O)OR⁵, —OC(O)R⁵, —C(O)R⁵, —SO₂NR³R⁴, —NR³SO₂R⁵, —SO₂R⁵, —NR³R⁴, or —OR⁵; and R³, R⁴, and R⁵ are each independently hydrogen, C₁-C₆ alkyl, C₁-C₆ haloalkyl, or C₃-C₈ cycloalkyl. In some embodiments, R²ᴬ and R²ᴮ are each independently hydrogen, halogen, C₁-C₆ alkyl, C₁-C₆ haloalkyl, —NHC(O)R⁵, or —OR⁵; and R⁵ is hydrogen, C₁-C₆ alkyl, C₁-C₆ haloalkyl, or C₃-C₈ cycloalkyl. In some embodiments, R²ᴬ and R²ᴮ are each independently hydrogen, halogen, C₁-C₆ alkyl, C₁-C₆ haloalkyl, —NHC(O)—C₁-C₆ alkyl, —O—C₁-C₆ alkyl, —O—C₁-C₆ haloalkyl, or —O—C₃-C₈ cycloalkyl. In some embodiments, R²ᴬ and R²ᴮ are each independently hydrogen, halogen, C₁-C₄ alkyl, C₁-C₄ haloalkyl, —NHC(O)—C₁-C₄ alkyl, —O—C₁-C₄ alkyl, —O—C₁-C₄ haloalkyl, or —O—C₃-C₆ cycloalkyl. The halogen of R²ᴬ or R²ᴮ can be F, Cl, Br, or I. The C₁-C₄ alkyl of R²ᴬ or R²ᴮ, alone or as a part of another group, can be methyl, ethyl, propyl, isopropyl, butyl, isobutyl, sec-butyl, or tert-butyl. The C₁-C₄ haloalkyl of R²ᴬ or R²ᴮ, alone or as a part of another group, can be difluoromethyl, trifluoromethyl, fluoromethyl, 2,2,2-trifluoroethyl. The —O—C₃-C₆ cycloalkyl of R²ᴬ or R²ᴮ can be —O— cyclopropyl, —O— cyclobutyl, —O-cyclopentyl, or —O-cyclohexyl. In some embodiments, R²ᴬ and R²ᴮ are each independently H, F, Me, —CF₃, —NHC(O)Me, —NHC(O)Et, —OMe, —OCHF₂, —OCF₃, or —O— cyclopentyl. In some embodiments, R²ᴬ and R²ᴮ are each independently H, F, Me, —NHC(O)Me, —NHC(O)Et, —OMe, —OCHF₂, or —O-cyclopentyl. In some embodiments, R²ᴬ and R²ᴮ are each independently H, F, —OMe, or —O-cyclopentyl. In some embodiments, R²ᴬ is —O-cyclopentyl and R²ᴮ is H, F, or —OMe. In some embodiments, R²ᴬ is —O-cyclopentyl and R²ᴮ is —OMe.

In some embodiments, R²ᴬ and R²ᴮ together form a 3-6 membered heterocycle having 1-2 heteroatoms selected from N, O, and S, which is optionally substituted with oxo. In some embodiments, R²ᴬ and R²ᴮ together form a 3-6 membered heterocycle having at least one nitrogen atom, which is optionally substituted with oxo. In some embodiments, R²ᴬ and R²ᴮ together form azetidine, pyrrolidine, piperidine azetidin-2-one, pyrrolidin-2-one, or piperidin-2-one. In some embodiments, R²ᴬ and R²ᴮ together form pyrrolidin-2-one. In some embodiments, R²ᴬ, R²ᴮ, and phenyl together form indolin-2-one.

In some embodiments, the compound of formula I-1 or 1-3 is a compound of formula I-1a:

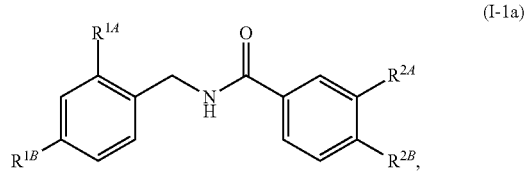

(I-1a)

wherein R₁ᴬ, R₁ᴮ, R²ᴬ, and R²ᴮ are as defined and described herein.

In some embodiments, the compound of formula I-2 is a compound of formula I-2a:

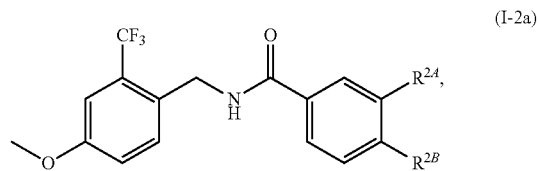

(I-2a)

wherein R²ᴬ and R²ᴮ are as defined and described herein.

In some embodiments, R²ᴬ is hydrogen, —NHC(O)—C₁-C₆ alkyl, or —O—C₃-C₈ cycloalkyl. In some embodiments, R²ᴬ is —O—C₃-C₈ cycloalkyl. In some embodiments, R²ᴬ is —O— cyclopentyl. In some embodiments, R²ᴮ is hydrogen, halogen, C₁-C₆ alkyl, —NHC(O)—C₁-C₆ alkyl, —O—C₁-C₆ alkyl, or —O—C₁-C₆ haloalkyl. In some embodiments, R²ᴮ is H, F, or —OMe.

Exemplified compounds of formula I-3, I-1a, or I-2a are listed in Table 1.

TABLE 1

Compounds of formula I-3, I-1a, or I-2a

| ID | Structure |
|---|---|
| 1 | 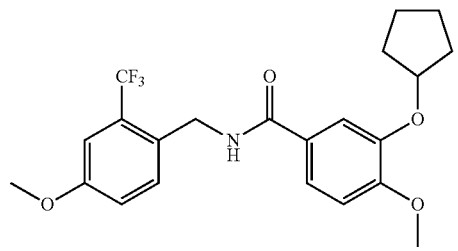 [SMILES: COc1ccc(CNC(=O)c2ccc(OC)c(OC3CCCC3)c2)c(C(F)(F)F)c1] |
| 2 | 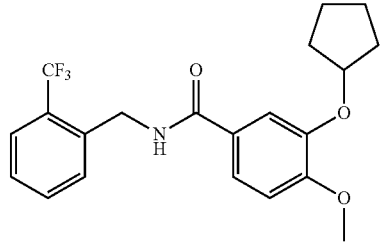 [SMILES: COc1ccc(C(=O)NCc2ccccc2C(F)(F)F)cc1OC1CCCC1] |
| 3 | 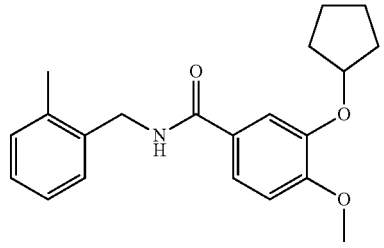 [SMILES: COc1ccc(C(=O)NCc2ccccc2C)cc1OC1CCCC1] |
| 4 | 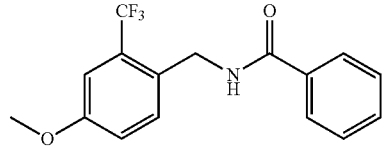 [SMILES: COc1ccc(CNC(=O)c2ccccc2)c(C(F)(F)F)c1] |

TABLE 1-continued

Compounds of formula I-3, I-1a, or I-2a

| ID | Structure |
|---|---|
| 5 | 2-CF3, 4-methoxybenzyl N-(4-fluorobenzamide) |
| 6 | 2-CF3, 4-methoxybenzyl N-(3-acetamidobenzamide) |
| 7 | 2-CF3, 4-methoxybenzyl N-(3-propionamidobenzamide) |
| 8 | 2-CF3, 4-methoxybenzyl N-(3-acetamido-4-methylbenzamide) |
| 9 | 2-CF3, 4-methoxybenzyl N-(2-oxoindoline-6-carboxamide) |
| 10 | 2-CF3, 4-methoxybenzyl N-(4-acetamidobenzamide) |
| 11 | 2-CF3, 4-methoxybenzyl N-(4-methoxybenzamide) |
| 14 | 2-CF3, 4-methoxybenzyl N-(4-(difluoromethoxy)benzamide) |
| 19 | 2-CF3, 4-methoxybenzyl N-(3-(cyclopentyloxy)benzamide) |
| 20 | 2-CF3, 4-methoxybenzyl N-(3-(cyclopentyloxy)-4-fluorobenzamide) |

In some embodiments, the compound of formula I-2a is selected from the group consisting of:

[structures shown], and

In some embodiments, ring A is piperidinyl. In some embodiments, the compound of formula I is a compound of formula I-4:

$$\text{(I-4)}$$

$(R^1)_m$ — [benzyl-NH-C(O)-piperidinyl-N-$R^{2C}$]

wherein $R^{2C}$ is hydrogen, $C_1$-$C_6$ alkyl, $C_1$-$C_6$ haloalkyl, —C(O)N$R^3R^4$, —C(O)O$R^5$, —C(O)$R^5$, —SO$_2$N$R^3R^4$, or —SO$_2R^5$; $R^3$, $R^4$, and $R^5$ are each independently hydrogen, $C_1$-$C_6$ alkyl, $C_1$-$C_6$ haloalkyl, or $C_3$-$C_8$ cycloalkyl; and $R^1$ and subscript m are as defined and described herein.

In some embodiments, $R^{2C}$ is hydrogen, $C_1$-$C_6$ alkyl, $C_1$-$C_6$ haloalkyl, —C(O)O$R^5$, or —C(O)$R^5$; and $R^5$ is hydrogen, $C_1$-$C_6$ alkyl, $C_1$-$C_6$ haloalkyl, or $C_3$-$C_8$ cycloalkyl. In some embodiments, $R^{2C}$ is hydrogen, $C_1$-$C_6$ alkyl, —C(O)O—C$_1$-C$_6$ alkyl, —C(O)—C$_1$-C$_6$ alkyl, or —C(O)—C$_3$-C$_8$ cycloalkyl. In some embodiments, R$^{2C}$ is hydrogen, C$_1$-C$_4$ alkyl, —C(O)O—C$_1$-C$_4$ alkyl, —C(O)—C$_1$-C$_4$ alkyl, or —C(O)—C$_3$-C$_6$ cycloalkyl. The C$_1$-C$_4$ alkyl of R$^{2C}$, alone or as a part of another group, can be methyl, ethyl, propyl, isopropyl, butyl, isobutyl, sec-butyl, or tert-butyl. The —C(O)—C$_3$-C$_6$ cycloalkyl of R$^{2C}$ can be —C(O)-cyclopropyl, —C(O)-cyclobutyl, —C(O)— cyclopentyl, or —C(O)-cyclohexyl. In some embodiments, R$^{2C}$ is H, ethyl, propyl sec-butyl, —C(O)O$^t$Bu, —C(O)Et, —C(O)Pr, or —C(O)-cyclopropyl. In some embodiments, R$^{2C}$ is —C(O)Et or —C(O)-cyclopropyl. In some embodiments, R$^{2C}$ is —C(O)Et.

In some embodiments, the compound of formula I-4 is a compound of formula I-1b:

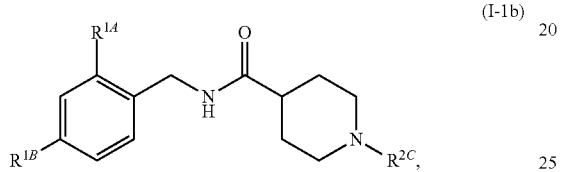

(I-1b)

wherein R$^{1A}$, R$^{1B}$, and R$^{2C}$ are as defined and described herein.

In some embodiments, the compound of formula I-4 is a compound of formula I-2b:

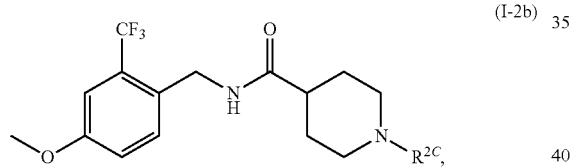

(I-2b)

wherein R$^{2C}$ is as defined and described herein.

Exemplified compounds of formula I-2b are listed in Table 2.

TABLE 2

Compounds of formula I-2b

| ID | Structure |
| --- | --- |
| 21 | 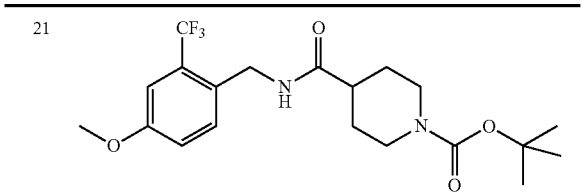 |
| 22 | 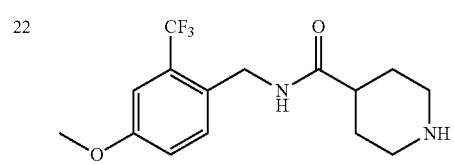 |

TABLE 2-continued

Compounds of formula I-2b

| ID | Structure |
| --- | --- |
| 23/ RBH61 | 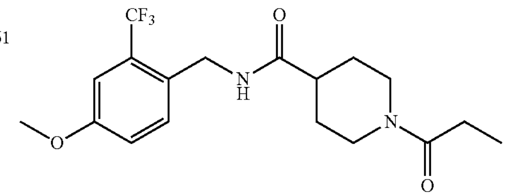 |
| 24 | 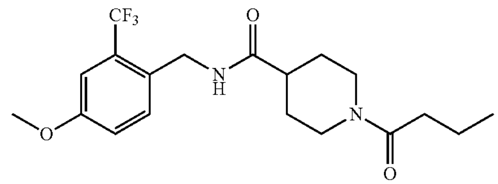 [SMILES: CCCC(=O)N1CCC(C(=O)NCc2ccc(OC)cc2C(F)(F)F)CC1] |
| 25 | 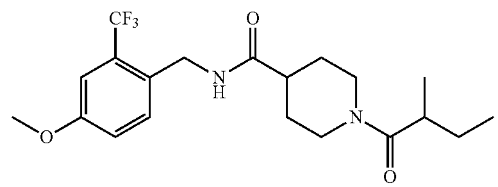 [SMILES: CCC(C)C(=O)N1CCC(C(=O)NCc2ccc(OC)cc2C(F)(F)F)CC1] |
| 26 | 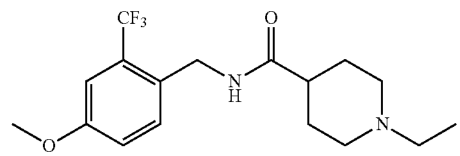 [SMILES: CCN1CCC(C(=O)NCc2ccc(OC)cc2C(F)(F)F)CC1] |
| 27 | 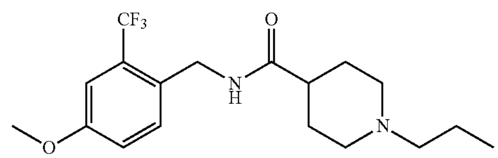 [SMILES: CCCN1CCC(C(=O)NCc2ccc(OC)cc2C(F)(F)F)CC1] |
| 28 | 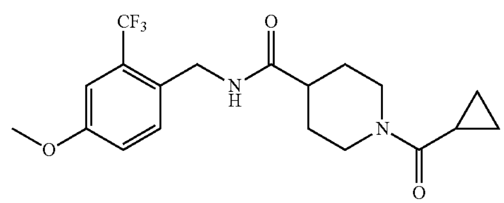 [SMILES: COc1ccc(CNC(=O)C2CCN(C(=O)C3CC3)CC2)c(C(F)(F)F)c1] |

In some embodiments, R$^{2C}$ is —C(O)Et. In some embodiments, the compound of formula I-2b has the formula:

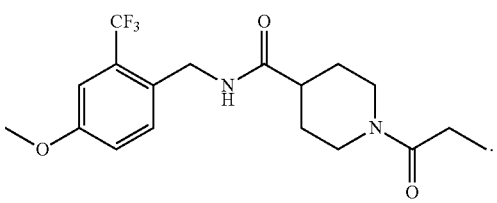 [SMILES: CCC(=O)N1CCC(C(=O)NCc2ccc(OC)cc2C(F)(F)F)CC1]

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (e.g. (+)-tartrates, (−)- tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another. In some embodiments of formula I-2a wherein $R^{2A}$, $R^{2B}$, and phenyl together form indolin-2-one, compounds of the following formulae can exist in equilibrium:

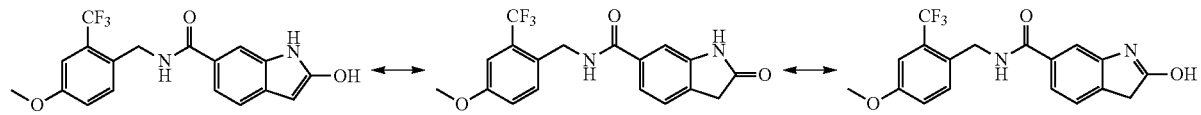 [SMILES: COc1ccc(CNC(=O)c2ccc3cc(O)[nH]c3c2)c(C(F)(F)F)c1 ; COc1ccc(CNC(=O)c2ccc3c(c2)NC(=O)C3)c(C(F)(F)F)c1 ; COc1ccc(CNC(=O)c2ccc3c(c2)N=C(O)C3)c(C(F)(F)F)c1]

able acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensul- Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be labeled with radioactive or stable isotopes, such as for example deuterium ($^2$H), tritium ($^3$H), iodine-125 ($^{125}$I), fluorine-18 ($^{18}$F), nitrogen-15 ($^{15}$N), oxygen-17 ($^{17}$O), oxygen-18 ($^{18}$O), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

VI. Compositions

In a second aspect, the present invention provides a pharmaceutical composition including the compound of formula I and one or more pharmaceutically acceptable excipients. In some embodiments, the pharmaceutical composition includes the compound of formula I and one or more pharmaceutically acceptable excipients. In some embodiments, the pharmaceutical composition includes the compound of formula I-2a and one or more pharmaceutically acceptable excipients. In some embodiments, the pharmaceutical composition includes the compound of formula I-2b and one or more pharmaceutically acceptable excipients.

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and the anti-inflammatory sEH/PDE4 dual inhibitor of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the anti-inflammatory the anti-inflammatory sEH/PDE4 dual inhibitor of Formula I.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the anti-inflammatory sEH/PDE4 dual inhibitor of Formula I mixed with a filler or binders such as lactose or starches, lubricants such as talc or magnesium stearate, and, optionally, stabilizers. In soft capsules, the anti-inflammatory sEH/PDE4 dual inhibitor of Formula I may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the anti-inflammatory sEH/PDE4 dual inhibitor of Formula I are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the anti-inflammatory sEH/PDE4 dual inhibitor of Formula I in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropyl-methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol monooleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the anti-inflammatory sEH/PDE4 dual inhibitor of Formula I in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The compositions of the present invention and compositions of the invention can also be delivered as microspheres for slow release in the body. For example, microspheres can be formulated for administration via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J Pharm. Pharmacol.* 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J Hosp. Pharm.* 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

The pharmaceutical formulations of the compounds of formula I of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The pharmaceutical formulations of the compounds of formula I of the invention can be provided as a salt and can be formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

The pharmaceutical preparation is preferably in unit dosage form. In such form the preparation is subdivided into unit doses containing appropriate quantities of the anti-inflammatory glucocorticosteroid and/or the GR modulator of Formula I. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, etc. Suitable dosage ranges for the compound of the present invention include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

The compounds of the present invention can be co-administered with another active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, i.e., preparing a single pharmaceutical composition including both the compound of the present invention and the active agent. In other embodiments, the compound of the present invention and the active agent can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

IV. Methods

In a third aspect, the present invention provides a method of inhibiting soluble epoxide hydrolase (sEH) and phosphodiesterase 4 (PDE4). The method includes contacting the soluble epoxide hydrolase (sEH) and phosphodiesterase 4 (PDE4) with an effective amount of the compound of formula I, or the pharmaceutical composition including the compound of formula I, thereby inhibiting the soluble epoxide hydrolase (sEH) and phosphodiesterase 4 (PDE4).

In a fourth aspect, the present invention provides a method of treating an inflammatory disease. The method includes administering to a subject in need thereof a therapeutically effective amount of the compound of formula I, or the pharmaceutical composition including the compound of formula I, thereby treating the inflammatory disease.

In some embodiments, the inflammatory disease is inflammation, pain, hypertension, depression, psoriasis, psoriatic arthritis, chronic obstructive pulmonary disease (COPD), or asthma.

In some embodiments, the present invention provides methods of inhibiting the function of soluble epoxide hydrolase (sEH), which metabolizes epoxy-fatty acids such as epoxyeicosatrienoic acids (EETs) to their corresponding diols, called dihydroxy eicosatrienoic acid (DHETs). In some embodiments, inhibition of sEH elevates EET levels. In an exemplary embodiment, the method includes contacting the soluble epoxide hydrolase (sEH) with an effective amount of the compound of formula I, or the pharmaceutical composition thereof and detecting a change in sEH activity. In some embodiments, the method includes contacting the soluble epoxide hydrolase (sEH) with an effective amount of the compound of formula I, or the pharmaceutical composition thereof, thereby reducing or inhibiting the sEH activity. In some embodiments, the method includes contacting the soluble epoxide hydrolase (sEH) with an effective amount of the compound of formula I, or the pharmaceutical composition thereof, thereby reducing or inhibiting the sEH activity, in turn stabilizing or increasing the level of epoxyeicosatrienoic acids (EETs).

In some embodiments, the present invention provides methods of inhibiting the function of phosphodiesterase 4 (PDE4), which is the major enzyme degrading cyclic adenosine monophosphate (cAMP) into 5-AMP. In some embodiments, inhibition of PDE4 increases cAMP levels. In an exemplary embodiment, the method includes contacting the phosphodiesterase 4 (PDE4) with an effective amount of the compound of formula I, or the pharmaceutical composition thereof and detecting a change in PDE4 activity. In some embodiments, the method includes contacting the phosphodiesterase 4 (PDE4) with an effective amount of the compound of formula I, or the pharmaceutical composition thereof, thereby reducing or inhibiting the PDE4 activity. In some embodiments, the method includes contacting the phosphodiesterase 4 (PDE4) with an effective amount of the compound of formula I, or the pharmaceutical composition thereof, thereby reducing or inhibiting the PDE4 activity, in turn increasing the level of cyclic adenosine monophosphate (cAMP). In some embodiments, the method includes contacting the phosphodiesterase 4 (PDE4) with an effective amount of the compound of formula I, or the pharmaceutical composition thereof and detecting a change of cyclic adenosine monophosphate (cAMP).

The compound of formula I can be a dual sEH/PDE4 inhibitor. In some embodiments, the present invention provides methods of inhibiting the function of soluble epoxide hydrolase (sEH) and phosphodiesterase 4 (PDE4). In some embodiments, inhibition of sEH elevates EET levels and inhibition of PDE4 increases cAMP levels. In an exemplary embodiment, the method includes contacting the soluble epoxide hydrolase (sEH) and phosphodiesterase 4 (PDE4) with an effective amount of the compound of formula I, or the pharmaceutical composition thereof and detecting a change in both sEH and PDE4 activity. In some embodiments, the method includes contacting the soluble epoxide hydrolase (sEH) and phosphodiesterase 4 (PDE4) with an effective amount of the compound of formula I, or the pharmaceutical composition thereof, thereby inhibiting both sEH and PDE4 activity. In some embodiments, the method includes contacting the soluble epoxide hydrolase (sEH) and phosphodiesterase 4 (PDE4) with an effective amount of the compound of formula I, or the pharmaceutical composition thereof, thereby inhibiting both sEH and PDE4 activity, in turn stabilizing or increasing the level of epoxyeicosatrienoic acids (EETs) and increasing the level of cyclic adenosine monophosphate (cAMP). In some embodiments, the method includes contacting the soluble epoxide hydrolase (sEH) and phosphodiesterase 4 (PDE4) with an effective amount of the compound of formula I, the pharmaceutical composition thereof, and detecting a change of cyclic adenosine monophosphate (cAMP).

Soluble epoxide hydrolase (sEH) plays a major role in the in vivo metabolism of endogenous lipid epoxides, such as the EETs and squalene oxide, a key intermediate in the synthesis of cholesterol. EETs are lipid signalling molecules that function in an autocrine and paracrine manner. These lipids play a role in asthma, pain, and inflammation. The EETs have been found to have anti-inflammatory and vasoactive properties. By reducing sEH epoxide hydrolase activity, and thereby shutting off the major route of metabolism of the EETs, the levels of these molecules can be stabilized or increased, subsequently increasing blood flow and reducing hypertension. This reduction in sEH activity can be achieved in genetic models in which sEH has been knocked out, or through the use of small molecule sEH inhibitors. In some embodiments, the reduction in sEH activity is achieved by contacting the soluble epoxide hydrolase (sEH) with an effective amount of the compound of formula I.

Through metabolism of EETs and other lipid mediators, sEH plays a role in several diseases, including hypertension, cardiac hypertrophy, arteriosclerosis, brain and heart ischemia/reperfusion injury, cancer and pain.

Inflammation is part of the complex biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and initiate tissue repair. The five classical signs of inflammation are heat, pain, redness, swelling, and loss of function.

Hypertension (HTN or HT), also known as high blood pressure (HBP), is a long-term medical condition in which the blood pressure in the arteries is persistently elevated. High blood pressure usually does not cause symptoms. Long-term high blood pressure, however, is a major risk factor for coronary artery disease, stroke, heart failure, atrial fibrillation, peripheral vascular disease, vision loss, chronic kidney disease, and dementia.

Ventricular hypertrophy (VH) is thickening of the walls of a ventricle (lower chamber) of the heart. Although left ventricular hypertrophy (LVH) is more common, right ventricular hypertrophy (RVH), as well as concurrent hypertrophy of both ventricles can also occur.

Arteriosclerosis is the thickening, hardening and loss of elasticity of the walls of arteries. This process gradually restricts the blood flow to one's organs and tissues and can lead to severe health risks brought on by atherosclerosis, which is a specific form of arteriosclerosis caused by the buildup of fatty plaques, cholesterol, and some other substances in and on the artery walls.

Reperfusion injury or reperfusion insult, sometimes called ischemia-reperfusion injury (IRI) or reoxygenation injury, is the tissue damage caused when blood supply returns to tissue (re-+perfusion) after a period of ischemia or lack of oxygen (anoxia or hypoxia). The absence of oxygen and nutrients from blood during the ischemic period creates a condition in which the restoration of circulation results in inflammation and oxidative damage through the induction of oxidative stress rather than (or along with) restoration of normal function. The ischemia/reperfusion injury can occur in brain and/or heart.

PDE4 is an intracellular enzyme that promotes production of proinflammatory mediators and decreases production of anti-inflammatory mediators. Phosphodiesterase 4 (PDE4) promotes inflammation by degrading intracellular levels of cyclic adenosine monophosphate (cAMP), a naturally occurring second messenger that helps maintain immune homeostasis. PDE4 degradation of cAMP can cause immune cell activation and the release of proinflammatory mediators such as TNF-α, IL-17, and IFN-γ. By breaking down cAMP, PDE4 indirectly decreases the production of anti-inflammatory mediators such as IL-10. PDE4 has been implicated in a number of inflammatory diseases, including psoriasis, psoriatic arthritis, and ankylosing spondylitis.

Phosphodiesterase 4 (PDE4) is the predominant enzyme that degrades the second messenger cAMP in many immune cells, including eosinophils, neutrophils, macrophages, T cells, and monocytes. Proinflammatory mediators released by those cells lead to activation of and tissue infiltration by other immune cells, as well as activation and hyperproliferation of keratinocytes; this process could play a role in the development of psoriatic lesions. Evidence suggests that cAMP causes a down regulatory signal in immune cells, thus suppressing the production of proinflammatory mediators, including tumor necrosis factor (TNF)-$\alpha$, interleukin (IL)-17, and interferon (IFN)-$\gamma$. It is also believed that cAMP promotes the production of anti-inflammatory mediators such as IL-10.

Psoriasis and psoriatic arthritis are associated with aberrant inflammation and the production of proinflammatory mediators. Psoriasis and psoriatic arthritis are inflammatory diseases with overlapping features and shared immunologic mechanisms. Psoriasis is a systemic disease in that it primarily affects the skin but up to 40% of individuals with psoriasis may go on to develop psoriatic arthritis. Psoriatic arthritis typically affects the peripheral joints and can occasionally affect the spine and sacroiliac area. Enthesitis, dactylitis, and nail changes such as pitting and discoloration are also common manifestations of psoriatic disease in patients with joint involvement.

Psoriasis (PsO) is a chronic inflammatory disease of the skin. Inflammation is a tightly regulated, naturally occurring part of the body's protective response to injury or infection, intended to prevent damage to surrounding tissue. In response to inflammation, several mechanisms work to regulate this immune response. Thus, these regulatory mechanisms help to establish immune homeostasis.

The most common form of psoriasis, plaque psoriasis, manifests as well-demarcated, raised, scaly, erythematous skin lesions. These lesions can appear anywhere on the body but are most commonly found on the scalp, elbows, nails, lower back, and knees.

Psoriasis plaque formation is thought to be caused by dysregulated immune activity within the skin. This dysregulation can lead to an imbalance and overproduction of proinflammatory cytokines such as TNF-$\alpha$, IL-17, and IL-23 from immune cells. These cytokines promote chronic inflammation of the epidermis and induce keratinocyte hyperproliferation. These changes result in redness, itching, epidermal thickening and scaly plaques.

PDE4 is an intracellular enzyme, located within immune cells, which plays an important role in modulating the overproduction of these proinflammatory cytokines. PDE4 is the predominant intracellular cAMP-degrading enzyme within a variety of inflammatory cells, including eosinophils, neutrophils, macrophages, T cells, and monocytes. PDE4 degrades cAMP into its inactive form AMP, thus allowing these immune cells to produce elevated levels of proinflammatory cytokines and decreased levels of anti-inflammatory cytokines. Overproduction of proinflammatory cytokines is thought to drive the hyperproliferation and altered differentiation of keratinocytes. These changes can produce epidermal thickening and result in raised, red, scaly, and sometimes itchy psoriatic lesions (plaque psoriasis).

Psoriatic arthritis (PsA) is an inflammatory arthritis associated with psoriasis and characterized by stiffness, pain, swelling, and tenderness of the joints and surrounding ligaments and tendons (dactylitis and enthesitis). Studies have confirmed that increased levels of proinflammatory mediators are found in psoriatic lesions and the synovium of patients with PsA.

In psoriatic arthritis, abnormal levels of multiple proinflammatory and anti-inflammatory mediators have been observed in B cells, Chondrocytes, and Synovial cells.

Intracellular cAMP is degraded by the enzyme PDE4, which leads to the increased production of proinflammatory mediators and decreased production of anti-inflammatory mediators. Once an immune cell has been activated, it releases proinflammatory mediators that can then activate other immune cells and promote cell proliferation, thus recruiting more immune cells to the site of disease. In psoriatic disease, this process does not resolve; instead, it disrupts immune homeostasis, thus creating a chronic cycle of inflammation.

PDE4 plays an important role in the regulation of the pro- and anti-inflammatory mediators that are involved in psoriatic arthritis. Dysregulation of the production of pro- and anti-inflammatory mediators in joint-resident cells in the synovium could account for the characteristic swelling and tenderness of PsA.

With regard to COPD, PDE 4 is the primary cAMP-hydrolyzing enzyme in inflammatory and immune cells, especially macrophages, eosinophils, and neutrophils, all of which are found in the lungs of COPD and asthma patients. Inhibition of PDE 4 leads to elevated cAMP levels in these cells, down-regulating the inflammatory response.

PDE 4 has also attracted much attention because it is expressed in airway smooth muscle. In vitro, PDE 4 inhibitors relax lung smooth muscle (Undem et al 1994; Dent and Giembycz 1995). In COPD and asthma, a selective PDE4 inhibitor with combined bronchodilatory and anti-inflammatory properties would seem desirable.

In some embodiments, the method includes administering one or more second agents (e.g. therapeutic agents). In some embodiments, the method includes administering one or more second agents (e.g. therapeutic agents) in a therapeutically effective amount. In some embodiments, the second agent is an agent known to be useful in inhibiting a sEH and/or PDE4. In some embodiments, the second agent is an agent for treating an inflammatory disease. In some embodiments, the inflammatory disease is inflammation, pain, hypertension, depression, psoriasis, psoriatic arthritis, chronic obstructive pulmonary disease (COPD), or asthma. In some embodiments, the second agent is an agent for treating inflammation. In some embodiments, the second agent is an agent for treating pain. In some embodiments, the second agent is an agent for treating hypertension. In some embodiments, the second agent is an agent for treating psoriasis or psoriatic arthritis. In some embodiments, the second agent is an agent for treating chronic obstructive pulmonary disease (COPD). In some embodiments, the second agent is an agent for treating asthma. In some embodiments, the second agent is an anti-inflammatory agent. In some embodiments, the second agent is a sEH inhibitor. In some embodiments, the second agent is a PDE4 inhibitor.

V. Examples

Example 1: General Chemical Methods

Example 1.1: Chemicals and Reagents

All reagents and solvents were purchased from commercial suppliers and were used directly without further purification. All reactions were carried out at room temperature unless otherwise specified. Reactions were monitored by thin-layer chromatography (TLC) on Merck $F_{254}$ silica gel 60 aluminum sheets, and spots were revealed with UV light (254 mm), potassium permanganate or Ninhydrin stains.

Example 1.2: Instrumentation and Sample Analysis $^1$H NMR spectra were recorded on a 400 MHz Bruker Avance III HD Nanobay Spectrometer with deuterated chloroform (CDCl$_3$; δ=7.24 ppm) or deuterated dimethyl sulfoxide (DMSO-d$_6$) containing TMS as internal standard. $^{13}$C NMR spectra were recorded on a Bruker Avance III HD Nanobay spectrometer at 100 MHz. The purity of the inhibitors reported in this manuscript were determined by HPLC-UV using Agilent 1200 series HPLC system equipped with Phenomenex Luna2 C18 reverse phase column (C18, 4.6 mm×150 mm, 5 μm) coupled with Agilent G1314 UV-vis detector (detection at 200, 210, 254 and 360) with solvent gradient acetonitrile/water 20 to 95% over 15 min. HRMS spectra were recorded on Thermo Electron LTQ-Orbitrap XL Hybrid MS in ESI mode.

Example 1.3: Dual Drug Design and Structural Development

The design of dual modulators requires a combination of two pharmacophores in one novel molecule. The right choice of template inhibitors is essential. As shown in FIG. 1, the first dual inhibitor (dual-i) design was started with the sEH inhibitor (sEH-i) GSK 2256294 and the PDE4 inhibitor (PDE4-i) Rolipram. GSK 2256294 was chosen by its successful phase I clinical trial and the subnanomolar IC$_{50}$ value on recombinant protein [Refs. 16 and 17]. Rolipram was selected based on the previously discovered synergism with sEH inhibition in pain treatment [Ref. 1]. Efficiency of Rolipram analogues having more bulky functional groups in place of pyrrolidone, such as Roflumilast, as well as literature cocrystal structures of PDE4 with dialkoxyphenyl family of inhibitors [Ref. 18] were suggesting that there is enough space in PDE4 active site to accommodate larger substituents on dialkoxy phenyl ring of Rolipram. The 2-, 4-substituted benzyl amide moiety was abstracted from GSK 2256294 and combined with the 3-(cyclopentyloxy)-4-methoxybenzene moiety from Rolipram, leading to the first dual-i design. Within the first dual-i design, the 2-trifluoromethyl-4-methoxy substitution of the benzyl amide was evaluated by replacement. After comparing the first dual-i design with Apremilast, a FDA approved PDE4-i, a similarity of the core structure was recognized (in bold, FIG. 1). This similarity inspired the second dual-i design, in which the 3-(cyclopentyloxy)-4-methoxy substitution of the central benzene moiety was evaluated by replacement. After discarding the 3-(cyclopentyloxy)-4-methoxy benzene substitution, PDE4 inhibition was still achieved by the derivatives. This finding led to the assumption that the 4-methoxy benzyl amide moiety might be sufficient as PDE4 pharmacophore. Therefore, structural fragments were then introduced in the design improving the pharmacokinetic properties of the dual inhibitors. TPPU is an in house sEH-i with good bioavailability [Ref. 19]. To increase structural diversity and improve bioavailability the 1-(piperidin-1-yl)propan-1-one fragment of TPPU (sEH-i) was combined with the 2-trifluoro-4-methoxy benzyl amide moiety of the previous design, creating the third and final dual-i design. Several N-substitutions of the piperidine fragment were evaluated within this structural class.

Example 1.4: Synthetic Routes for Preparing sEH/PDE4 Dual Inhibitors

Scheme 1. Synthetic routes for the production of sEH/PDE4 dual inhibitors

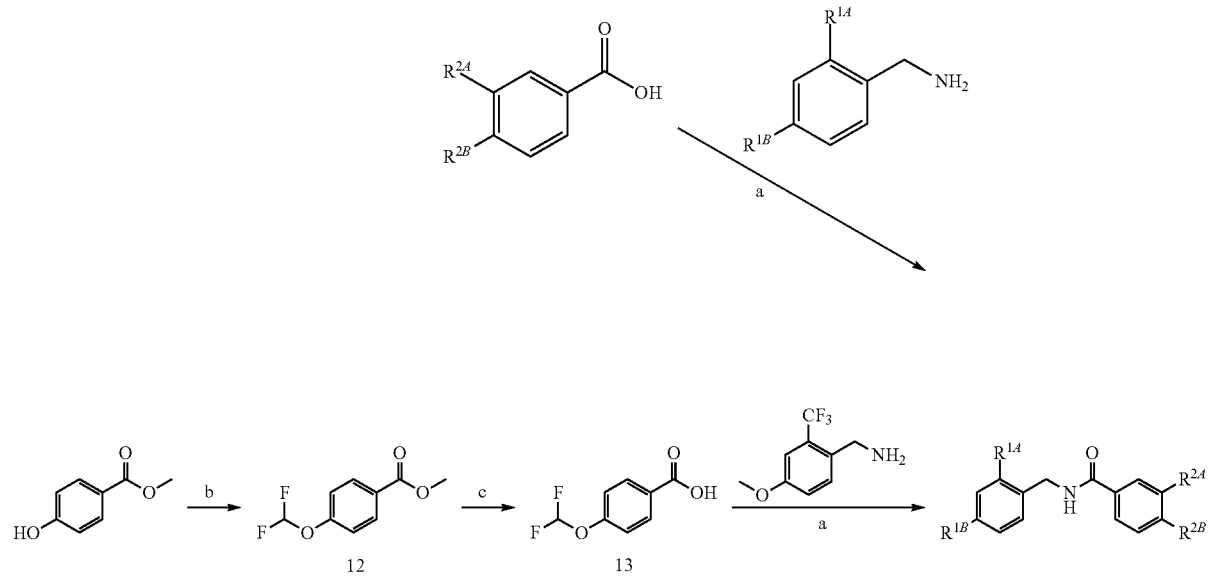

-continued

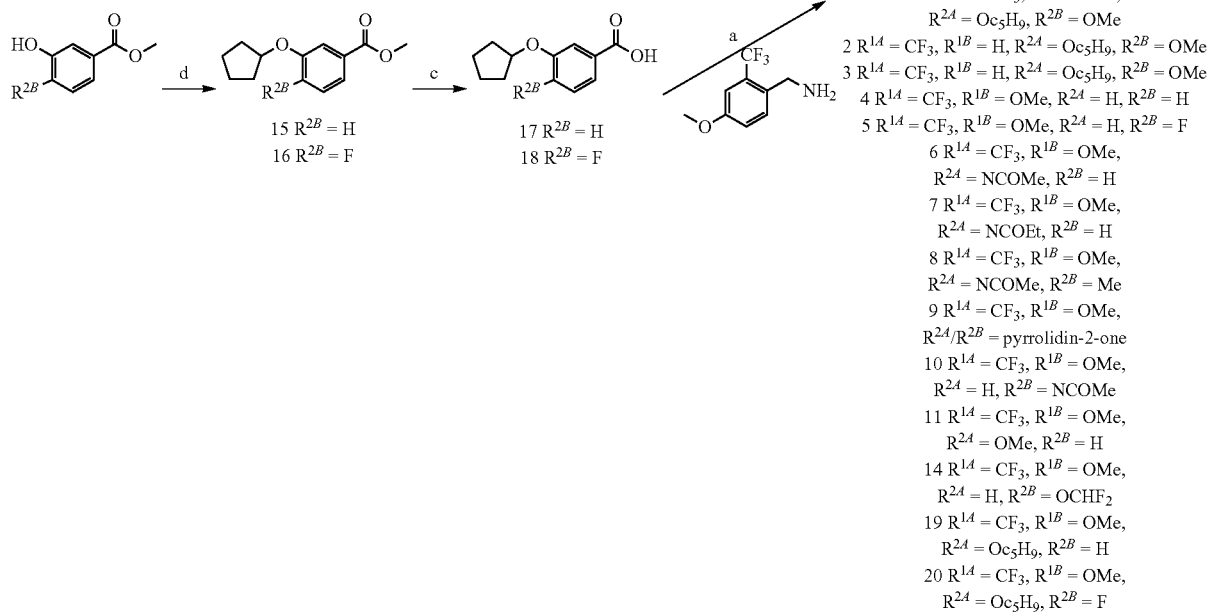

a) EDC, DMAP, DCM, 12 h; b) 1. Sodium chloro difluoro acetate, Cs$_2$CO$_3$, DMF, H$_2$O, 2 h; 2. 100° C., 12 h; c) NaOH, H$_2$O/THF/MeOH, 40° C., 12 h; d) Cyclopentyl bromide, K$_2$CO$_3$, KI, DMF, 65° C., 21 h

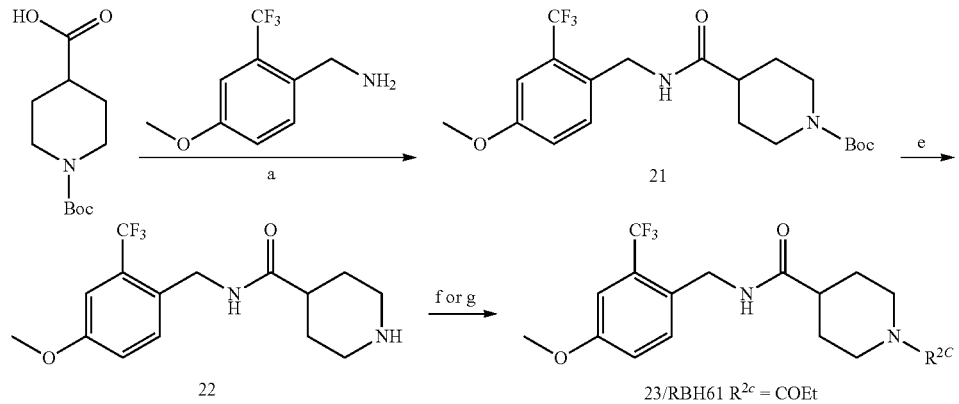

a) EDC, DMAP, DCM, 12 h; e) TFA, DCM, 12 h; f) Propionic acid or butanoic acid, 2-methylbutyric acid, or cyclopropanecarbocylic acid, (COCl)$_2$, DCM, TEA, 4 h; g) MeI or EtI. K$_2$CO$_3$, DMF, 12 h Scheme 1 shows the synthetic pathways toward sEH/PDE4 dual modulators. A central method was the amide synthesis. In general a benzoic acid derivative or a piperidine carboxylic acid derivative was activated with 1-ethyl-3-(3-dimethylaminopropyl)carbodiimide and a catalytic amount of 4-dimethylaminopyridine under dry conditions, followed by the addition of a benzylamine derivative to produce compounds 1-11, 14 and 19-21 [Ref. 3]. Benzoic acids used for the synthesis of compounds 14 and 19-20 were prepared as described below. To introduce the 2-difluoromethoxy substitution, methyl 4-hydroxy benzoate and sodium chloro difluoro acetate were reacted under basic condition and gave, after decarboxylation, 4-(difluoromethoxy)benzoic acid methyl ester (12) [Ref. 20]. After an ester hydrolysis the substituted benzoic acid (13) was used for the final amide synthesis step. For the preparation of the 3-(cyclopentyloxy)benzoic acid (17) and 3-(cyclopentyloxy)-4-fluorobenzoic acid (18), 4-fluoro substituted and non-substituted 3-hydroxy methyl benzoates were reacted with cyclopentyl bromide under basic conditions in presence of a catalytic amount of potassium iodide to generate the cyclopentyloxy substituted intermediates 15 and 16 [Ref. 12]. Again after ester hydrolysis the benzoic acid derivatives 17 and 18 were used for the final amide coupling step. The synthesis of the piperidine containing inhibitors started with preparation of the intermediate 21. Deprotection of the amine was performed with trifluoroacetic acid, delivering 22 [Ref. 21]. Two methods were used for the following final synthetic step, each depending on the required substitution. To introduce the amide substitution, appropriate acid chlorides were purchased or generated with oxalylchloride and further reacted with 22 under dry basic conditions to produce 23-25, and 28 [Ref. 22]. To synthesize the ethyl and propyl substituted piperidine derivatives (26, 27), 22 was reacted with ethyl iodide or propyl iodide under basic conditions.

Example 2: Preparation of Compound 12

Methyl 4-(difluoromethoxy)benzoate (12)

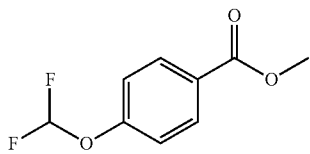

1 g (6.6 mmol) methyl 4-hydroxybenzoate, 4.3 g (13 mmol) cesium carbonate and 2.5 g (16 mmol) sodium chloro difluoro acetate were dissolved in 48 ml dimethylformamide and 7 ml water under a nitrogen atmosphere. The mixture was first stirred for 15 min at rt and subsequently heated to 100° C. for 2 h. After completion of the reaction, the mixture was diluted with 50 mL of water and the product extracted with 100 mL of dichloromethane. The organic phase was dried over magnesium sulfate and evaporated under reduced pressure. The product was used in the next step without further purification. Yield: 0.47 g (35%). $^1$H NMR (400 MHz, DMSO-$d_6$) δ 8.02 (d, J=8.9 Hz, 2H), 7.40 (s, 1H), 7.30 (d, J=8.8 Hz, 2H), 3.85 (s, 3H).

Example 3: Preparation of Compounds 15 and 16

Shown on the Preparation of methyl 3-(cyclopentyloxy)benzoate (15) (Method 15)

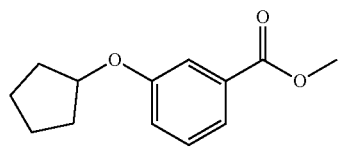 [SMILES: COC(=O)c1cccc(OC2CCCC2)c1]

1 g (6.6 mmol) of methyl 3-hydroxybenzoate, 22 mg (0.13 mmol) of potassium iodide and 1.4 g (9.9 mmol) of potassium carbonate are stirred in 6.5 ml of dimethylformamide at 65° C. Subsequently 0.92 ml (8.6 mmol) of bromocyclopentane was added dropwise. The reaction was further stirred for 21 h, cooled down to rt and diluted with 50 ml dichloromethane, washed with aqueous sodium hydroxide solution (2 M, 3×50 mL) and brine (50 mL). The organic solvent was dried over magnesium sulfate and evaporated under reduced pressure. The product was used in the next step without further purification. Yield: 1.1 g (76%). $^1$H NMR (400 MHz, DMSO-$d_6$) δ 7.85-7.03 (m, 4H), 4.87 (tt, J=5.9, 2.5 Hz, 1H), 3.84 (s, 3H), 2.16-1.42 (m, 8H).

Methyl 3-(cyclopentyloxy)-4-fluorobenzoate (16)

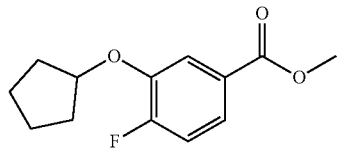 [SMILES: COC(=O)c1ccc(F)c(OC2CCCC2)c1]

Compound 16 was prepared according to Method 15. Yield: 1 g (70%). $^1$H NMR (400 MHz, DMSO-$d_6$) δ 8.00-6.91 (m, 3H), 5.18-4.68 (m, 1H), 3.85 (s, 3H), 2.20-1.37 (m, 8H).

Example 4: Preparation of Compounds 13, 17 and 18

Shown on the Preparation of 4-(difluoromethoxy)benzoic acid (13) (Method 13)

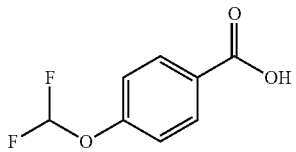 [SMILES: O=C(O)c1ccc(OC(F)F)cc1]

0.47 g (2.3 mmol) methyl 4-(difluoromethoxy)benzoate (12) and 0.47 g (12 mmol) sodium hydroxide were stirred in a mixture of 10 ml of tetrahydrofuran, 10 ml of methanol and 5 ml of water under a nitrogen atmosphere at 40° C. for 12 h. The organic solvents were removed under reduced pressure and the remaining aqueous phase was acidified through dropwise addition of concentrated hydrochloric acid solution. The precipitated product was filtered, dried and used in the next step without further purification. Yield: 0.18 (41%). $^1$H NMR (400 MHz, DMSO-$d_6$) δ 13.02 (s, 1H), 8.00 (d, J=8.8 Hz, 2H), 7.39 (s, 1H), 7.32-7.25 (m, 2H).

3-(Cyclopentyloxy)benzoic acid (17)

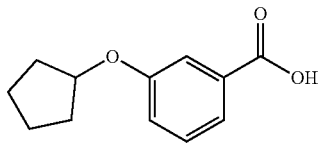 [SMILES: O=C(O)c1cccc(OC2CCCC2)c1]

Compound 17 was prepared according to Method 13. Yield: 0.4 g (85%). $^1$H NMR (400 MHz, DMSO-$d_6$) δ 12.95 (s, 1H), 7.92-6.80 (m, 4H), 5.02-4.59 (m, 1H), 2.12-1.48 (m, 8H).

3-(Cyclopentyloxy)-4-fluorobenzoic acid (18)

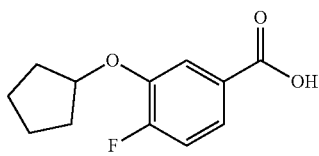 [SMILES: O=C(O)c1ccc(F)c(OC2CCCC2)c1]

Compound 18 was prepared according to Method 13. Yield: 0.8 g (71%). $^1$H NMR (400 MHz, DMSO-d$_6$) δ 13.06 (s, 1H), 7.95-6.87 (m, 3H), 4.99-4.90 (m, 1H), 2.02-1.54 (m, 8H).

Example 5: Preparation of Compounds 1-11, 14 and 19-20

Shown on the Preparation of 3-(cyclopentyloxy)-4-methoxy-N-(4-methoxy-2-(trifluoromethyl)benzyl) benzamide (1) (Method 1)

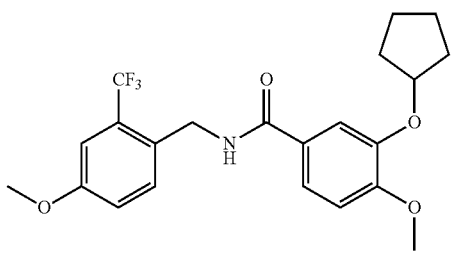 [SMILES: COc1ccc(CNC(=O)c2ccc(OC)c(OC3CCCC3)c2)c(C(F)(F)F)c1]

0.2 g (0.85 mmol) of 3-(cyclopentyloxy)-4-methoxybenzoic acid, 160 mg (1 mmol) of 1-ethyl-3-(3-dimethylaminopropyl)carbodiimide and 20 mg (0.17 mmol) 4-(dimethylamino)pyridine were dissolved in 10 ml dichloromethane and stirred under a nitrogen atmosphere for 1 h. Subsequently, 160 μl (0.93 mmol) (4-methoxy-2-(trifluoromethyl)phenyl)methanamine was added to the mixture. The reaction was further stirred for 12 h. After completion of the reaction, dichloromethane was removed under reduced pressure. The residue was dissolved in 20 ml of ethyl acetate and washed with aqueous sodium hydroxide solution (2 M, 3×20 mL), aqueous hydrochloric acid solution (2 M, 3×20 mL) and brine (20 mL). The organic solvent was dried over magnesium sulfate and removed under reduced pressure. The crude product was purified by recrystallization from ethyl acetate and hexane mixture. The pure product remained as a white solid. Yield: 0.18 g (50%). $^1$H NMR (400 MHz, Chloroform-d) δ 7.86-6.25 (m, 6H), 4.89-4.81 (m, 1H), 4.74 (d, J=6.1, 1.3 Hz, 2H), 3.89 (s, 3H), 3.85 (s, 3H), 2.33-1.20 (m, 8H); $^{13}$C-NMR (DMSO-d$_6$) δ 166.7, 157.1, 151.3, 147, 128.2, 128, 127.8, 126.9, 126.4, 124.1, 121.3, 118.2, 115.1, 112.6, 109.3, 80.1, 55.2, 54.1, 42.7, 31.7, 30.6, 24.1, 23.7; HRMS: measured [M+Cl]$^-$ 374.1523 (calculated: 374.1521).

3-(Cyclopentyloxy)-4-methoxy-N-(2-(trifluoromethyl)benzyl)benzamide (2)

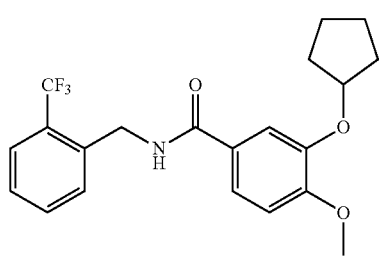

Compound 2 was prepared according to Method 1. Yield: 0.16 (49%). $^1$H NMR (400 MHz, Chloroform-d) δ 7.90-6.47 (m, 7H), 4.88-4.84 (m, 1H), 4.82 (d, J=6.4 Hz, 2H), 3.89 (s, 3H), 2.08-1.50 (m, 8H); $^{13}$C-NMR (DMSO-d$_6$) δ 168.3, 156.1, 148.3, 147.5, 127.2, 127, 126.9, 126.7, 126.5, 123.4, 120.3, 119.2, 116.3, 112.1, 108.3, 79.1, 53.1, 41.7, 33.7, 31.4, 25.1, 23.1; HRMS: measured [M+Cl]$^-$ 428.1239 (calculated: 428.1237).

3-(Cyclopentyloxy)-4-methoxy-N-(2-methylbenzyl) benzamide (3)

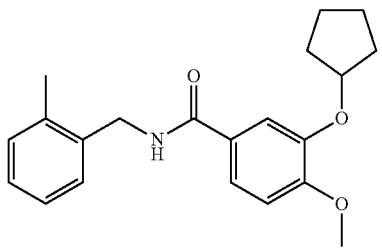 [SMILES: COc1ccc(C(=O)NCc2ccccc2C)cc1OC1CCCC1]

Compound 3 was prepared according to Method 1. Yield: 0.15 (62%). $^1$H NMR (400 MHz, Chloroform-d) δ 7.63-6.07 (m, 7H), 4.93-4.81 (m, 1H), 4.65 (d, J=5.4 Hz, 2H), 3.89 (s, 3H), 2.40 (s, 3H), 2.08-1.54 (m, 8H); $^{13}$C-NMR (DMSO-d$_6$) δ 167.3, 155.1, 147.3, 146.5, 128.1, 128, 127.9, 125.7, 120.8, 119.1, 117.3, 113.1, 109.3, 79.5, 52.1, 42.7, 31.7, 30.4, 24.1, 22.1, 19.1; HRMS: measured [M+Cl]$^-$ 458.1344 (calculated: 458.1342).

N-(4-Methoxy-2-(trifluoromethyl)benzyl)benzamide (4)

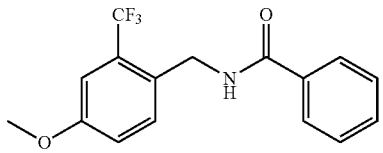 [SMILES: COc1ccc(CNC(=O)c2ccccc2)c(C(F)(F)F)c1]

Compound 4 was prepared according to Method 1. Yield 0.11 g (34%). $^1$H NMR (400 MHz, Chloroform-d) δ 7.36 (m, 8H), 6.40 (s, 1H), 3.7 (s, 3H); $^{13}$C-NMR (DMSO-d$_6$) δ 166.1, 158.1, 150.2, 146, 127.8, 127.6, 127.3, 126.9, 126.1, 123.1, 120.3, 119.2, 116.1, 112.6, 109.1, 53.1, 40.7, HRMS: measured [M+HCOO]$^-$ 354.0950 (calculated: 354.0953).

4-Fluoro-N-(4-methoxy-2-(trifluoromethyl)benzyl) benzamide (5)

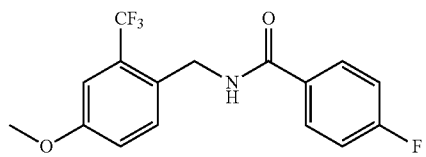 [SMILES: COc1ccc(CNC(=O)c2ccc(F)cc2)c(C(F)(F)F)c1]

Compound 5 was prepared according to Method 1. Yield: 0.21 g (66%). $^1$H NMR (400 MHz, DMSO-d$_6$) δ 9.05 (t, J=5.8 Hz, 1H), 8.26-6.91 (m, 7H), 4.58 (d, J=5.7 Hz, 2H), 3.82 (s, 3H); $^{13}$C-NMR (DMSO-d$_6$) δ 168.1, 155.1, 148.2, 147, 130.8, 129.6, 129.7, 128.9, 128.1, 126.1, 125.1, 120.1,

3-Acetamido-N-(4-methoxy-2-(trifluoromethyl)benzyl)benzamide (6)

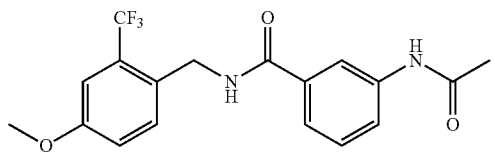 [SMILES: COc1ccc(CNC(=O)c2cccc(NC(C)=O)c2)c(C(F)(F)F)c1]

Compound 6 was prepared according to Method 1. Yield: 0.23 mg (56%). ¹H NMR (400 MHz, DMSO-$d_6$) δ 10.05 (s, 1H), 8.94 (t, J=5.8 Hz, 1H), 8.24-6.44 (m, 7H), 4.52 (d, J=5.6 Hz, 2H), 3.77 (s, 3H), 2.00 (s, 3H); ¹³C-NMR (DMSO-$d_6$) δ 166.9, 159.1, 151.2, 145, 141.3, 128.6, 127.4, 127.3, 127.1, 126.8, 122.1, 121.3, 118.3, 117.1, 112.6, 109.7, 55.8, 42.6; HRMS: measured [M−H]⁻ 365.1114 (calculated: 365.1113).

N-(4-Methoxy-2-(trifluoromethyl)benzyl)-3-propionamidobenzamide (7)

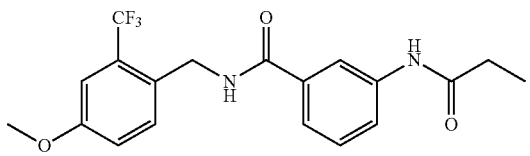 [SMILES: CCC(=O)Nc1cccc(C(=O)NCc2ccc(OC)cc2C(F)(F)F)c1]

Compound 7 was prepared according to Method 1. Yield: 0.14 (41%). ¹H NMR (400 MHz, DMSO-$d_6$) δ 10.08 (s, 1H), 9.04 (t, J=5.9 Hz, 1H), 8.13-7.01 (m, 7H), 4.63 (d, J=5.6 Hz, 2H), 3.88 (s, 3H), 2.40 (q, J=7.5 Hz, 2H), 1.15 (t, J=7.5 Hz, 3H); ¹³C-NMR (DMSO-$d_6$) δ 167.9, 155.1, 150.2, 146, 142.3, 129.6, 128.5, 128.3, 128.2, 128, 121.1, 119.3, 118.1, 116.1, 110.6, 109.7, 56.8, 41.6, 10.1; HRMS: measured [M+HCOO]⁻ 425.1320 (calculated: 425.1321).

3-Acetamido-N-(4-methoxy-2-(trifluoromethyl)benzyl)-4-methylbenzamide (8)

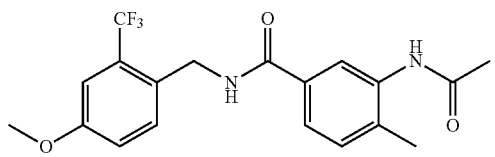 [SMILES: COc1ccc(CNC(=O)c2ccc(C)c(NC(C)=O)c2)c(C(F)(F)F)c1]

Compound 8 was prepared according to Method 1. Yield: 0.1 g (29%). ¹H NMR (400 MHz, DMSO-$d_6$) δ 9.43 (s, 1H), 8.95 (t, J=5.8 Hz, 1H), 8.32-6.80 (m, 6H), 4.57 (d, J=5.6 Hz, 2H), 3.82 (s, 3H), 2.25 (s, 3H), 2.08 (s, J=2.7 Hz, 3H). ¹³C-NMR (DMSO-$d_6$) δ 166, 158.1, 152.2, 146, 142.3, 128.3, 128.1, 128, 127.8, 121.1, 120.3, 119.3, 118.1, 112.7, 109.9, 56.8, 40.6, 17.3; HRMS: measured [M+HCOO]⁻ 435.1321 (calculated: 435.1321).

N-(4-Methoxy-2-(trifluoromethyl)benzyl)-2-oxoindoline-6-carboxamide (9)

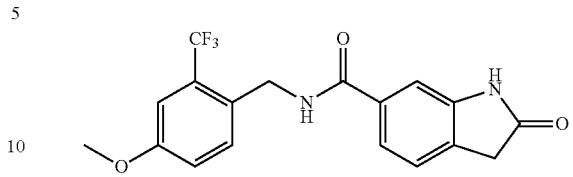

Compound 9 was prepared according to Method 1. Yield: 0.14 (44%). ¹H NMR (400 MHz, DMSO-$d_6$) δ 10.56 (s, 1H), 9.00 (t, J=5.8 Hz, 1H), 7.79-6.95 (m, 6H), 4.57 (d, J=5.6 Hz, 2H), 3.82 (s, 3H), 3.55 (s, 2H); ¹³C-NMR (DMSO-$d_6$) δ 176.7, 167.8, 155.1, 147.2, 141, 127, 126.9, 126.8, 126.6, 126.1, 124, 123.5, 120.1, 119.7, 118.1, 113.6, 109.6, 52.1, 42.7, 36.5; HRMS: measured [M+HCOO]⁻ 409.1008 (calculated: 409.1007).

4-Acetamido-N-(4-methoxy-2-(trifluoromethyl)benzyl)benzamide (10)

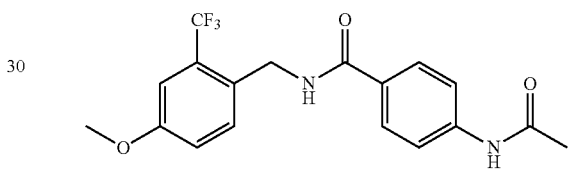

Compound 10 was prepared according to Method 1. Yield: 0.16 (50%). ¹H NMR (400 MHz, DMSO-$d_6$) δ 10.23 (s, 1H), 8.95 (t, J=5.8 Hz, 1H), 8.14-7.11 (m, 7H), 4.63 (d, J=5.6 Hz, 2H), 3.87 (s, 3H), 2.14 (s, 3H); ¹³C-NMR (DMSO-$d_6$) δ 166.3, 157.1, 152.2, 147, 142.3, 128.6, 128.5, 128.3, 127.9, 123.1, 122.3, 119.3, 118.1, 112.8, 109.3, 56.8, 41.6; HRMS: measured [M−H]⁻ 365.1111 (calculated: 365.1113).

4-Methoxy-N-(4-methoxy-2-(trifluoromethyl)benzyl)benzamide (11)

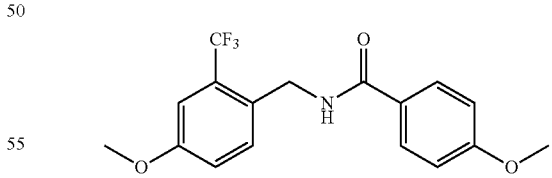

Compound 11 was prepared according to Method 1. Yield: 0.16 g (48%). ¹H NMR (400 MHz, DMSO-$d_6$) δ 8.88 (t, J=5.8 Hz, 1H), 8.17-7.73 (m, 2H), 7.57-7.33 (m, 1H), 7.32-7.14 (m, 2H), 7.09-6.92 (m, 2H), 4.57 (d, J=5.7 Hz, 2H), 3.83 (s, 3H), 3.82 (s, 3H); ¹³C-NMR (DMSO-$d_6$) δ 167.7, 156.1, 150.3, 148, 129.2, 128, 127.9, 127.7, 127.4, 123.1, 120.3, 119.2, 116.1, 113.6, 109.1, 56.2, 53.1, 41.7; HRMS: measured [M+HCOO]⁻ 384.1055 (calculated: 384.1057).

4-(Difluoromethoxy)-N-(4-methoxy-2-(trifluoromethyl)benzyl)benzamide (14)

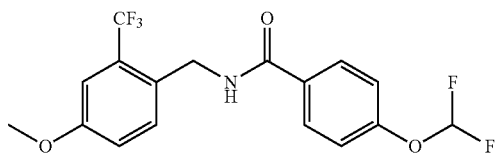 [SMILES: COc1ccc(CNC(=O)c2ccc(OC(F)F)cc2)c(C(F)(F)F)c1]

Compound 14 was prepared according to Method 1. Yield: 0.11 g (37%). $^1$H NMR (400 MHz, DMSO-$d_6$) δ 9.05 (t, J=5.7 Hz, 1H), 8.05-7.92 (m, 2H), 7.47-7.43 (m, 1H), 7.36 (s, 1H), 7.32-7.26 (m, 2H), 7.26-7.20 (m, 2H), 4.58 (d, J=5.6 Hz, 2H), 3.82 (s, 3H); $^{13}$C-NMR (DMSO-$d_6$) δ 167.8, 167.3, 167.1, 166.9, 157.1, 152.3, 148.3, 128.2, 128.1, 128, 127.9, 127.6, 123.2, 121.3, 119.1, 117.1, 112.6, 109.1, 50.1, 42.7; HRMS: measured [M−H]$^-$ 374.0813 (calculated: 374.0811).

3-(Cyclopentyloxy)-N-(4-methoxy-2-(trifluoromethyl)benzyl)benzamide (19)

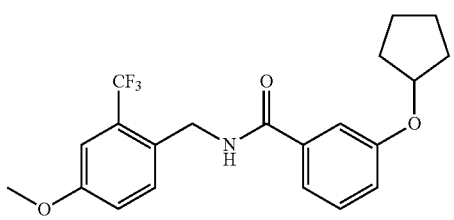 [SMILES: COc1ccc(CNC(=O)c2cccc(OC3CCCC3)c2)c(C(F)(F)F)c1]

Compound 19 was prepared according to Method 1. Yield: 0.1 g (30%). $^1$H NMR (400 MHz, DMSO-$d_6$) δ 9.00 (t, J=5.8 Hz, 1H), 7.79-6.89 (m, 7H), 4.96-4.81 (m, 1H), 4.57 (d, J=5.7 Hz, 2H), 3.82 (s, 3H), 2.04-1.47 (m, 8H); $^{13}$C-NMR (DMSO-$d_6$) δ 167.1, 156.2, 151.1, 148, 128.4, 128.2, 128.1, 127.9, 127.2, 126.5, 123.9, 120.3, 119.2, 116.1, 113.6, 109.1, 80.2, 53.1, 41.7, 30.7, 30.6, 24.1, 23.7; HRMS: measured [M+HCOO]$^-$ 438.1527 (calculated: 438.1528).

3-(Cyclopentyloxy)-4-fluoro-N-(4-methoxy-2-(trifluoromethyl)benzyl)benzamide (20)

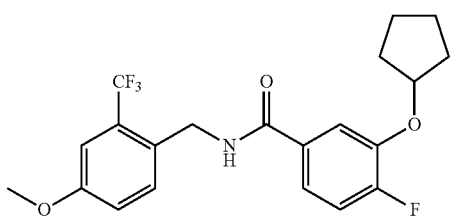 [SMILES: COc1ccc(CNC(=O)c2ccc(F)c(OC3CCCC3)c2)c(C(F)(F)F)c1]

Compound 20 was prepared according to Method 1. Yield: 0.1 (33%). $^1$H NMR (400 MHz, DMSO-$d_6$) δ 9.04 (t, J=5.8 Hz, 1H), 7.82-7.09 (m, 7H), 4.95 (tt, J=5.9, 2.4 Hz, 1H), 4.59 (d, J=5.6 Hz, 2H), 3.82 (s, 3H), 2.12-1.50 (m, 8H)); $^{13}$C-NMR (DMSO-$d_6$) δ 166.9, 166.4; 155.2, 155.3, 152.1, 147, 128.5, 128.3, 128.2, 128, 127.5, 122.9, 120.1, 119.2, 117.1, 112.6, 109.7, 80.6, 52.7, 40.7, 30.6, 30, 24.3, 23.9; HRMS: measured [M−H]$^-$ 410.1379 (calculated: 410.1377).

Example 6: Preparation of Compounds 21 and 22 tert-Butyl 4-((4-methoxy-2-(trifluoromethyl)benzyl)carbamoyl)piperidine-1-carboxylate (21)

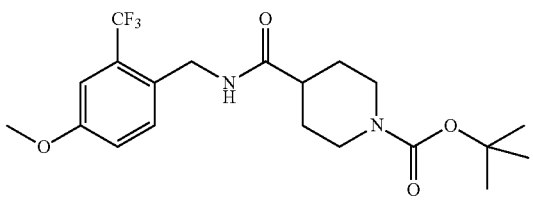 [SMILES: COc1ccc(CNC(=O)C2CCN(C(=O)OC(C)(C)C)CC2)c(C(F)(F)F)c1]

Compound 21 was prepared according to Method 1. Yield: 1.1 g (42%). $^1$H NMR (400 MHz, DMSO-$d_6$) δ 8.34 (t, J=5.8 Hz, 1H), 7.69-6.86 (m, 3H), 4.35 (d, J=5.6 Hz, 2H), 3.95 (d, J=13.2 Hz, 2H), 3.82 (s, 3H), 2.71 (d, J=24.0 Hz, 2H), 2.42-2.31 (m, 1H), 1.70 (d, J=13.2 Hz, 2H), 1.45 (d, J=4.2 Hz, 2H), 1.40 (s, 9H); $^{13}$C-NMR (DMSO-$d_6$) δ 173.9, 159.7, 158.8, 129.2, 126.5, 126.3, 126.2, 125.8, 123.8, 117.5, 109.2, 79.8, 55.8, 45.7, 45.2, 41.5, 38.9, 29.7, 29.6, 28.5, 28.3, 28.1; HRMS: measured [M+HCOO]$^-$ 461.1896 (calculated: 461.1895).

N-(4-Methoxy-2-(trifluoromethyl)benzyl)piperidine-4-carboxamide (22)

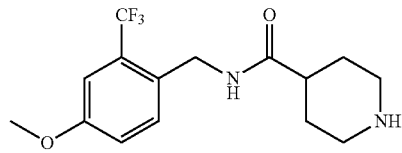 [SMILES: COc1ccc(CNC(=O)C2CCNCC2)c(C(F)(F)F)c1]

1.3 g (3 mmol) tert-Butyl 4-((4-methoxy-2-(trifluoromethyl)benzyl)carbamoyl)piperidine-1-carboxylate 21 and 2.8 mL (36 mmol) of trifluoroacetic acid were stirred in 16 mL of dichloromethane at 0° C. for 2 h. The organic phase was diluted with 4 mL dichloromethane and extracted with hydrochloric acid aqueous solution (10%, 3×20 mL). The aqueous layer was basified through the addition of solid sodium hydroxide pellets. From the basic aqueous layer the product was extracted with ethyl acetate (3×60 mL). The organic phase was dried over magnesium sulfate and evaporated. The remaining product was used in the next step without further purification. Yield: 0.73 g (77%). $^1$H NMR (400 MHz, DMSO-$d_6$) δ 8.27 (t, J=5.8 Hz, 1H), 7.81-6.84 (m, 3H), 4.34 (d, J=5.7 Hz, 2H), 3.82 (s, 3H), 2.99 (dt, J=12.3, 3.4 Hz, 2H), 2.66-2.45 (m, 3H), 1.76-1.32 (m, 4H); $^{13}$C-NMR (DMSO-$d_6$) δ 172.8, 158.7, 157.8, 128.4, 128.2, 128.1, 127.8, 125.3, 124.7, 123.9, 117.9, 109.1, 56.8, 44.7, 43.2, 41.7, 39.9, 29.4, 29.3; HRMS: measured [M+H]$^+$ 317.1493 (calculated: 317.1492).

Example 7: Preparation of Compounds 23/RBH61, 24, 25, and 28

Shown on the Preparation of N-(4-methoxy-2-(trifluoromethyl)benzyl)-1-propionylpiperidine-4-carboxamide 23/RBH61 (Method 23)

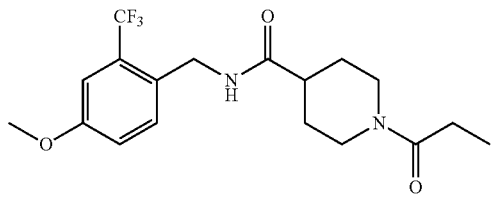 [SMILES: CCC(=O)N1CCC(C(=O)NCc2ccc(OC)cc2C(F)(F)F)CC1]

28 μL (0.38 mmol) of propionic acid and 40 μL (0.47 mmol) of oxalyl chloride were stirred in 1 mL of dry dichloromethane under a nitrogen atmosphere for 1 h, to generate propionyl chloride. In a separate flask 0.1 g (0.32 mmol) of N-(4-methoxy-2-(trifluoromethyl)benzyl)piperidine-4-carboxamide 22 and 80 μL (0.5 mmol) triethylamine were stirred in 2 ml of dry dichloromethane at 0° C. under a nitrogen atmosphere. The produced propionyl chloride solution was now added slowly to the amine containing reaction flask and the whole mixture was stirred for 4 h. The reaction was diluted with 7 mL of dichloromethane, washed with hydrochloric acid aqueous solution (2 M, 3×10 mL), sodium hydroxide aqueous solution (2 M, 3×10 mL) and brine (10 mL). The organic layer was dried over magnesium sulfate and evaporated under reduced pressure. The remaining crude material was purified by flash column chromatography (acetone/ethyl acetate=50:50). Yield: 70 mg (63%). $^1$H NMR (400 MHz, DMSO-$d_6$) δ 8.34 (t, J=5.8 Hz, 1H), 7.63-6.99 (m, 3H), 4.35 (d, J=6.0 Hz, 2H), 3.82 (s, 3H), 3.10-2.88 (m, 2H), 2.73-2.63 (m, 3H), 2.39-2.23 (m, 2H), 1.88-1.64 (m, 2H), 1.34-1.19 (m, 2H), 0.98 (t, J=7.4 Hz, 3H); $^{13}$C-NMR (DMSO-$d_6$) δ 176.9, 173.8, 156.5, 128.5, 128.2, 127.9, 127.8, 125.1, 124.8, 123.4, 118.7, 109.9, 56.9, 43.7, 42.2, 40.9, 38.9; 28.9, 28.8, 26.1, 10.2; HRMS: measured [M+FA]$^-$ 417.1633 (calculated: 417.1633).

1-Butyryl-N-(4-methoxy-2-(trifluoromethyl)benzyl)piperidine-4-carboxamide (24)

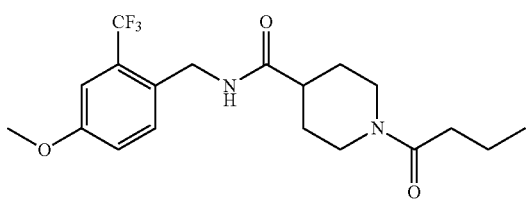 [SMILES: CCCC(=O)N1CCC(C(=O)NCc2ccc(OC)cc2C(F)(F)F)CC1]

Compound 24 was prepared according to Method 23. Yield: 0.05 g (37%). $^1$H NMR (400 MHz, DMSO-$d_6$) δ 8.35 (t, J=5.8 Hz, 1H), 7.53-7.04 (m, 3H), 4.35 (d, J=5.9 Hz, 2H), 3.94-3.85 (m, 1H), 3.82 (s, 3H), 3.01 (t, J=12.7 Hz, 2H), 2.71-2.55 (m, 1H), 2.28 (td, J=7.3, 3.1 Hz, 2H), 1.73 (t, J=7.4 Hz, 2H), 1.59-1.44 (m, 3H), 1.42-1.27 (m, 2H), 0.89 (t, J=7.4 Hz, 3H); $^{13}$C-NMR (DMSO-$d_6$) δ 176.7, 175.8, 155.5, 128.4, 128.2, 128, 127.9, 124.1, 124, 122.4, 119.7, 109.3, 54.9, 42.7, 41.2, 40.7, 37.9; 29.9, 28.8, 27.1, 19.2, 13.2; HRMS: measured [M−H]$^-$ 385.0268 (calculated: 385.0267).

N-(4-Methoxy-2-(trifluoromethyl)benzyl)-1-(2-methylbutanoyl)piperidine-4-carboxamide 25

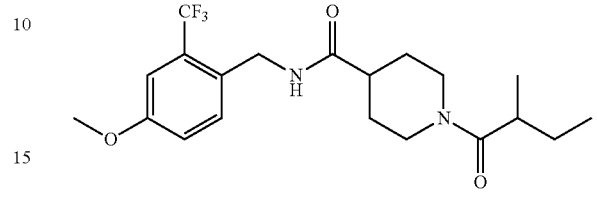

0.1 g (0.32 mmol) of N-(4-methoxy-2-(trifluoromethyl)benzyl)piperidine-4-carboxamide (22) and 44 μL (0.32 mmol) triethylamine were stirred in 5 mL dry dichloromethane at 0° C. under a nitrogen atmosphere. Subsequently, 39 μL (0.32 mmol) of 2-methylbutanoyl chloride was added and the reaction mixture was stirred for 4 h. The reaction was diluted with 5 mL of dichloromethane and washed with hydrochloric acid aqueous solution (2 M, 3×10 mL), sodium hydroxide aqueous solution (2 M, 3×10 mL) and once with 10 mL brine. The organic phase was dried over magnesium sulfate and removed under reduced pressure. The crude material was purified by flash column chromatography (acetone/ethyl acetate=50:50). Yield: 82 mg (65%). $^1$H NMR (400 MHz, DMSO-$d_6$) δ 8.37 (t, J=5.8 Hz, 1H), 7.49-7.09 (m, 3H), 4.39-4.48 (m, 1H), 4.37-4.34 (m, 2H), 4.07-3.95 (m, 1H), 3.82 (s, 3H), 3.1-2.96 (m, 1H), 2.71 (h, J=6.7 Hz, 1H), 2.58 (t, J=11.9 Hz, 1H), 2.47 (dd, J=11.5, 3.9 Hz, 1H), 1.83-1.7 (m, 2H), 1.62-1.21 (m, 2H), 0.97 (t, J=7.7 Hz, 3H), 0.81 (q, J=7.1 Hz, 3H); $^{13}$C-NMR (DMSO-$d_6$) δ 176.9, 175.7, 155.4, 128.3, 128.1, 128, 127.8, 125.2, 125.1, 123.4, 119.1, 109.2, 53.9, 42.5, 41, 40.2, 39.2, 37.9; 29.7, 27.5, 17.3, 10.2; HRMS: measured [M+HCOO]$^-$ 445.1947 (calculated: 445.1949).

1-(cyclopropanecarbonyl)-N-(4-methoxy-2-(trifluoromethyl)benzyl)piperidine-4-carboxamide (28)

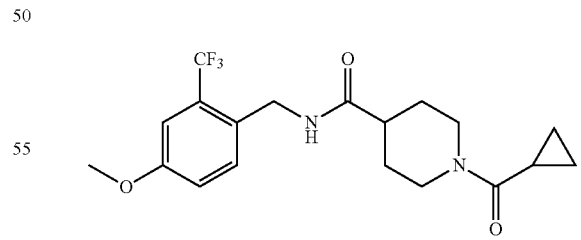

Compound 28 was prepared according to Method 23. Yield: 0.04 g (34%) $^1$H NMR (400 MHz, DMSO-$d_6$) δ 8.36 (t, 1H), 7.62-7.00 (m, 3H), 4.36 (d, J=5.9 Hz, 2H), 4.21-4.13 (m, 1H), 3.82 (s, 3H), 3.23-3.11 (m, 1H), 2.61 (s, 1H), 2.49-2.4 (m, 1H), 1.97 (td, J=7.0, 3.6 Hz, 2H), 1.88-1.30 (m, 5H), 0.70 (t, J=7.5 Hz, 4H). HRMS: measured [M−H]$^-$ 384.1660 (calculated: 384.1661).

Example 8: Preparation of Compounds 26 and 27

Shown on the Preparation of 1-ethyl-N-(4-methoxy-2-(trifluoromethyl)benzyl)piperidine-4-carboxamide 26 (Method 26)

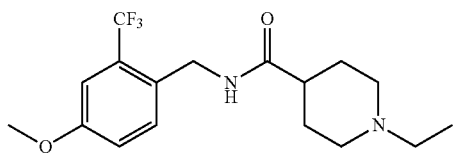 [SMILES: CCN1CCC(C(=O)NCc2ccc(OC)cc2C(F)(F)F)CC1]

0.15 g (0.48 mmol) of N-(4-methoxy-2-(trifluoromethyl)benzyl)piperidine-4-carboxamide 22, 0.13 g (0.95 mmol) of potassium carbonate and 38 μL (0.48 mmol) ethyl iodide were stirred in 3.2 mL of dimethylformamide for 24 h. After the reaction was completed, the pure product was precipitated with the addition of 2 M sodium hydroxide aqueous solution. Yield: 40 mg (24%). %). $^1$H NMR (400 MHz, DMSO-$d_6$) δ 8.13 (t, J=5.7 Hz, 1H), 7.66-6.43 (m, 3H), 4.12 (d, J=5.7 Hz, 2H), 3.72 (s, 3H), 3.31 (dt, J=12.1, 3.3 Hz, 2H), 2.67-2.48 (m, 3H), 1.77-1.42 (m, 4H), 3.02-2.98 (m, 2H), 0.95-1.16 (m, 3H); $^{13}$C-NMR (DMSO-$d_6$) δ 172.8, 158.7, 157.8, 128.2, 128.1, 127.8, 127.7, 125.3, 124.7, 123.9, 117.9, 109.1, 56.8, 49.9, 44.7, 43.2, 41.7, 39.9; 29.4, 29.3, 13.3; HRMS: measured [M+H]$^+$ 345.1814 (calculated: 345.1815).

N-(4-Methoxy-2-(trifluoromethyl)benzyl)-1-propylpiperidine-4-carboxamide 27

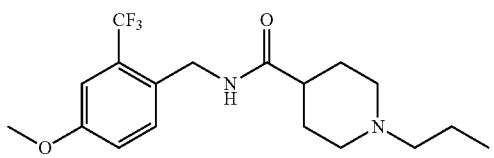 [SMILES: CCCN1CCC(C(=O)NCc2ccc(OC)cc2C(F)(F)F)CC1]

Compound 27 was prepared according to Method 26. Yield: 0.06 g (35%). $^1$H NMR (400 MHz, DMSO-$d_6$) δ 8.9 (t, J=5.7 Hz, 1H), 7.55-6.41 (m, 3H), 4.3 (d, J=5.8 Hz, 2H), 3.75 (s, 3H), 3.21 (dt, J=12.2, 2.9 Hz, 2H), 2.77-2.38 (m, 3H), 1.76-1.41 (m, 4H), 2.51-2.39 (m, 2H), 1.46-1.31 (m, 2H), 0.93-0.79 (m, 3H); $^{13}$C-NMR (DMSO-$d_6$) δ 173.8, 157.7, 156.8, 129.2, 128.6, 128.5, 128.3, 128.1, 125.7, 123.8, 117.6, 109.4, 59.3, 55.8, 47.9, 43.7, 42.2, 41.9, 39.7; 29.1, 21.2, 12.3; HRMS: measured [M+H]$^+$ 359.1970 (calculated: 359.1971).

Example 9: General Assay Methods

Example 9.1: sEH Activity Assay

The assay was performed as previously described [Ref. 26]. All hsEH and rsEH IC$_{50}$ values were determined by a fluorescence-based assay system of 96-well format. As substrate, non-fluorescent PHOME (3-phenylcyano-(6-methoxy-2-naphthalenyl)methyl ester 2-oxiraneacetic acid was used, which can be hydrolyzed by the sEH to the fluorescent 6-methoxynaphthaldehyde [Ref. 26]. The formation of the product was measured ($λ_{em}$=330 nm, $λ_{ex}$=465 nm) by a Tecan Infinite F200 Pro plate reader. All measurements were performed in triplicate.

Example 9.2: PDE4 Activity Assay

HEK293 cell culture and transfection: HEK293 cells were cultured in DMEM (Gibco life technologies) containing 10% FBS, 100 units/ml penicillin-streptomycin, and 2 mM L-glutamine. Cell transfections were performed with the PIE Transfection reagent (Qiagen) according to manufacturer's instructions.

Forster Resonance Energy Transfer (FRET):Measurements to track PKA activity. HEK293 cells were transfected with PM-AKAR3 plasmid DNA (a plasma membrane-targeted PKA activity reporter) according to methods described previously [Ref. 24]. Images were acquired using a Zeiss AXIO inverted fluorescence microscope (Carl Zeiss micrscopy, LLC, Thomwood, N.Y.) with a 40× oil-emersion objective lens and a charge-coupled device camera controlled by Metafluor software (Molecular Devices, Sunnyvale, Calif.). FRET was recorded by exciting the donor fluorophore at 430-455 nm and measuring emission fluorescence with two filters (475DF40 for cyan and 535DF25 for yellow). Images were subjected to background subtraction, and were acquired every 30 seconds with exposure time of 200 ms. The donor/acceptor FRET ratio was calculated and normalized to the ratio value of baseline. The binding of cAMP to AKAR3 increases YFP/CFP FRET ratio [Ref. 24].

Statistics: Statistical analysis was performed using GraphPad Prism 6 software (La Jolla, Calif.). Results are shown as mean±SEM and were analyzed by one way ANOVA with post hoc Bonferroni's multiple compression test.

Example 10: Water Solubility Approximation

Solutions of the compound under investigation were prepared in 0.1 M PBS buffer at pH 7.4 and 1% DMSO and placed in a 96-well transparent flat bottom microtiter plate. Precipitation of the compounds was measured at 650 nm using a microplate reader (Infinite M200).

Example 11: Pharmacology Methods

Example 11.1: PK Protocols for Pharmacokinetic Study in Rat

All the animal experiments were performed according to the protocols approved by the Animal Use and Care Committee of University of California-Davis. Male Sprague-Dawley rats (n=4, 8 week old, 250-300 g) were used in the pharmacokinetic study of sEH/PDE4 dual inhibitors. A cassette of four inhibitors (inhibitor 1, 19, 20 and 23/RBH61; 0.3 mg/kg per inhibitors, 0.9 to 1.2 mL) was given by oral gavage administration. Inhibitor was dissolved in 100% polyethylene glycol 300 to form a clear solution. Blood (10 μL) was collected from the tail vein by using a pipette tip rinsed with 7.5% EDTA(K3) at 0, 0.25, 0.5, 1, 2, 4, 8, 12, 24, 48 and 72 hour after oral dosing with the inhibitor. Each blood sample was immediately transferred to a tube containing 50 NL of water and mixed by Vortex for 1 min, all samples were stored at −80° C. until analysis. The blood samples were processed and sEH/PDE4 dual inhibitor concentrations determined, according to the previously reported method by Liu et al [Ref. 27].

Example 11.2: Exploration Assay

Each rat is placed in an open Plexiglas box with a floor area size of 40 cm×40 cm and a height of 30 cm. The floor area is marked with a 16 square grid. Over 2 min the rats exploration of the box is observed. A count of one is noted for each time the rat passes a square with its hind paws or lifts the front paws up on the sides of the box or does a similar movement within the box. Pre- and post-treated animals are compared to themselves and percent changes are determined.

Example 11.3: Evaluation of Inflammatory Pain Relief in Rat Model

The Hargreaves nociception assay was performed as previously described [Ref. 1]. The thermal withdrawal threshold was determined after oral gavage application of RBH61 (1, 3, 10 mg/kg), TPPU (1, 3 mg/kg), Rolipram (3 mg/kg), combination of TPPU+Rolipram (1.5+1.5 mg/kg, 3+3 mg/kg) in 500 μL 100% PEG300. Post oral gavage 0.2 μg/ml lipopolysaccharide (LPS) from *Escherichia coli* (0111:B4; Sigma Aldrich L2630) in 50 μl saline were injected intraplantar in the right back paw. Control animals received a 50 μl saline intraplantar sham injection in the right back paw.

Example 11.4: Statistics

Student t-test was performed in Microsoft Excel with a significance of P<0.05. Results are shown as mean±SD.

Example 12: In Vitro Evaluation of Compounds

TABLE 3

In vitro evaluation of sEH/PDE4 dual inhibitors 1-3

| ID | $R^{1A}$ | $R^{1B}$ | $IC_{50}(hsEH)^1$ [nM] | % cAMP increase rel. to Rolipram @ 1 μM$^2$ | w.s.$^3$ [μM] |
|---|---|---|---|---|---|
| Rolipram | — | — | >100000 | 100 | 750 |
| GSK2256294 | — | — | 0.027 | — | — |
| 1 | $CF_3$ | OMe | 0.6 ± 0.1 | 240 ± 14 | 37.5 |
| 2 | $CF_3$ | — | 15 ± 3 | 180 ± 12 | 37.5 |
| 3 | Me | — | 180 ± 40 | 200 ± 11 | 37.5 |

[1]The sEH $IC_{50}$ values are recorded on recombinant human sEH protein (hsEH);
[2]PDE4 inhibition is evaluated on cAMP increase in live HEK cells, transfected with a PKA biosensor and visualized relative to Rolipram at 1 μM;
[3]water solubility (w.s.) is measured in sodium phosphate buffer (0.1M, pH 7.4) with 1% DMSO.

In vitro profile of the first dual inhibitor 1 showed sEH $IC_{50}$ at subnanomolar concentration (0.6±0.1 nM), a cAMP increase of more than 200% compared to Rolipram at 1 μM and a moderate water solubility of 37.5 μM. Replacing 2-trifluoromethyl-4-methoxy benzyl substitution by simpler 2-trifluoromethyl and 2-methyl benzyl substituents resulted in significant drop in potency on both targets, while moderate water solubility stayed constant.

TABLE 4

In vitro evaluation of sEH/PDE4 dual inhibitors (4-11, 14, 19-20), second design

| ID | $R^{2B}$ | $R^{2A}$ | $IC_{50}(hsEH)^1$ [nM] | % cAMP increase rel. to Rolipram @ 1 μM$^2$ | w.s.$^3$ [μM] |
|---|---|---|---|---|---|
| 4 | — | — | 2 ± 0.9 | 160 ± 12 | 100 |
| 5 | F | — | 2.8 ± 0.4 | 110 ± 13 | 100 |
| 6 | — | NHCOMe | 2.9 ± 1.1 | 140 ± 15 | 100 |
| 7 | — | NHCOEt | 3.7 ± 1 | 150 ± 18 | 50 |
| 8 | Me | NHCOMe | 13 ± 2 | 140 ± 15 | 20 |
| 9 | pyrrolidin-2-one | | 3 ± 2 | 130 ± 25 | 100 |
| 10 | NHCOMe | — | 44 ± 5 | 100 ± 19 | 50 |
| 11 | OMe | — | 1 ± 0.2 | 160 ± 17 | 100 |
| 14 | $OCHF_2$ | — | 1.5 ± 0.4 | 150 ± 14 | 10 |
| 19 | — | $OcC_5H_9$ | 0.4 ± 0.1 | 147 ± 9 | 10 |
| 20 | F | $OcC_5H_9$ | 0.4 ± 0 | 222 ± 8 | 100 |

[1]The sEH $IC_{50}$ values are recorded on recombinant human sEH protein (hsEH);
[2]PDE4 inhibition is evaluated on cAMP increase in live HEK cells, transfected with a PKA biosensor and visualized relative to Rolipram at 1 μM;
[3]water solubility (w.s.) is measured in sodium phosphate buffer (0.1M, pH 7.4) with 1% DMSO.

Within the second structural class of dual sEH/PDE4 inhibitors the substitution pattern at the central benzene moiety was investigated. The first compound of this class, 4, contained a non-substituted central benzene fragment, resulting in a slight decrease of potency on both targets. Nevertheless, sEH $IC_{50}$ was in the low one digit nanomolar range and cAMP increase was 160±12% of Rolipram at 1 μM, while the water solubility improved up to 100 μM. Introduction of the fluorine substitution at position 4 of the benzene ring (5) only affected the PDE4 potency by lowering the cAMP increase to the level of Rolipram at 1 μM. Introduction of the N-acetamide substitution motive of the PDE4 inhibitor Apremilast in the meta position of the benzene moiety did not improve the potency of the compound (6) compared to the non-substituted inhibitor 4. Shifting the acetamide substitution in para position (10), elongating the substituent to propionamide (7) or introducing an additional methyl group in para position (8) decreased inhibition on both targets as well as water solubility. Thus the Apremilast inspired design did not improve the dual inhibitors. A para methoxy benzene substitution (11) also did not improve target inhibition compared to the non-substituted inhibitor (4), while the para difluoromethoxy benzene substituted inhibitor 14 even decreased water solubility to 10 μM. The meta cyclopentoxy benzene substitution in dual inhibitor 19 improved the sEH inhibition compared to the non-substituted inhibitor 4, but water solubility decreased by one order of magnitude and cAMP increase relative to Rolipram at 1 μM slightly decreased too. For inhibitor 20 the meta cyclopentyloxy benzene substitution was combined with a para fluoro benzene substituent in order to increase metabolic stability. The additional para fluoro substituent did not change sEH inhibition ($IC_{50}$ 0.4 nM), improved cAMP increase relative to Rolipram at 1 μM and restored the water solubility to 100 μM.

TABLE 5

In vitro evaluation of sEH/PDE4 dual inhibitors (21-27), third design

| ID | $R^{2C}$ | $IC_{50}(hsEH)^1$ [nM] | % cAMP increase rel. to Rolipram @ 1 $\mu M^2$ | w.s.$^3$ [$\mu M$] |
|---|---|---|---|---|
| TPPU$^4$ | — | 3.7 | 40 ± 10 | 200 |
| 21 | BOC | 1.7 ± 0.7 | 100 ± 12 | 100 |
| 22 | — | 370 ± 170 | 138 ± 5 | 1000 |
| 23/RBH61 | COEt | 2.1 ± 0.5 | 200 ± 19 | 100 |
| 24 | CO—$^n$Pr | 4 ± 2 | 110 ± 16 | 50 |
| 25 | CO—$^s$Bu | 7 ± 3 | 160 ± 11 | 0.5 |
| 26 | Et | 109 ± 16 | 60 ± 10 | 1000 |
| 27 | $^n$Pr | 190 ± 20 | 60 ± 14 | 1000 |
| 28 | CO-cyclopropyl | 1.4 ± 0.1 | 230 ± 15 | — |

$^1$The sEH IC$_{50}$ values are recorded on recombinant human sEH protein (hsEH);
$^2$PDE4 inhibition is evaluated on cAMP increase in live HEK cells transfected with a PKA biosensor and visualized relative to Rolipram at 1 $\mu$M;
$^3$water solubility (w.s.) is measured in sodium phosphate buffer (0.1M, pH 7.4) with 1% DMSO;
$^4$Literature value [Ref. 23].

The third structural class of dual sEH/PDE4 inhibitors enfolds in different N-substitution of the piperidine moiety. Dual inhibitor 22 contains a non-substituted piperidine, which led to a significant loss in sEH inhibitory potency ($IC_{50}$ 370±170 nM), a higher cAMP increase than Rolipram at 1 $\mu$M and an improved water solubility of 1 mM. Ethyl and propyl substituted modulators (26, 27) similarly had low sEH inhibitory potencies and high water solubility, but only 60% cAMP increase compared to Rolipram at 1 $\mu$M. Dual inhibitor 23 with a propionamide piperidine substitution showed a low one digit nanomolar sEH $IC_{50}$, 200% cAMP increase compared to Rolipram at 1 $\mu$M and 100 $\mu$M water solubility. Increasing the alkyl chain of the N-substitution to butyramide (24) and sec-butylamide (25) decreased sEH inhibition and even more dramatically water solubility.

Figure 2A:
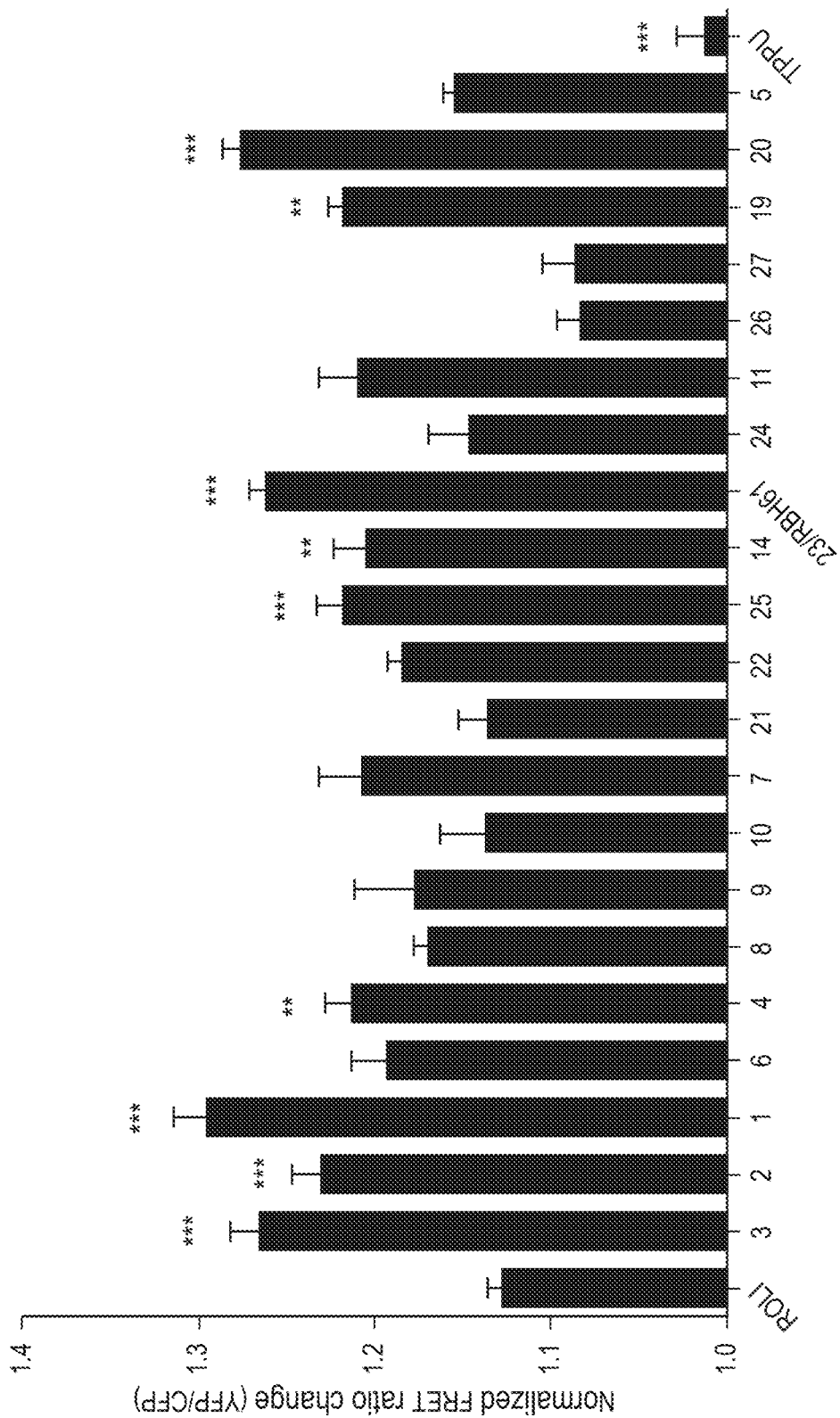
FIGS. 2A-2C show PKA activity generated by novel compounds using FRET biosensor in HEK293 cells.
Figure 2B:
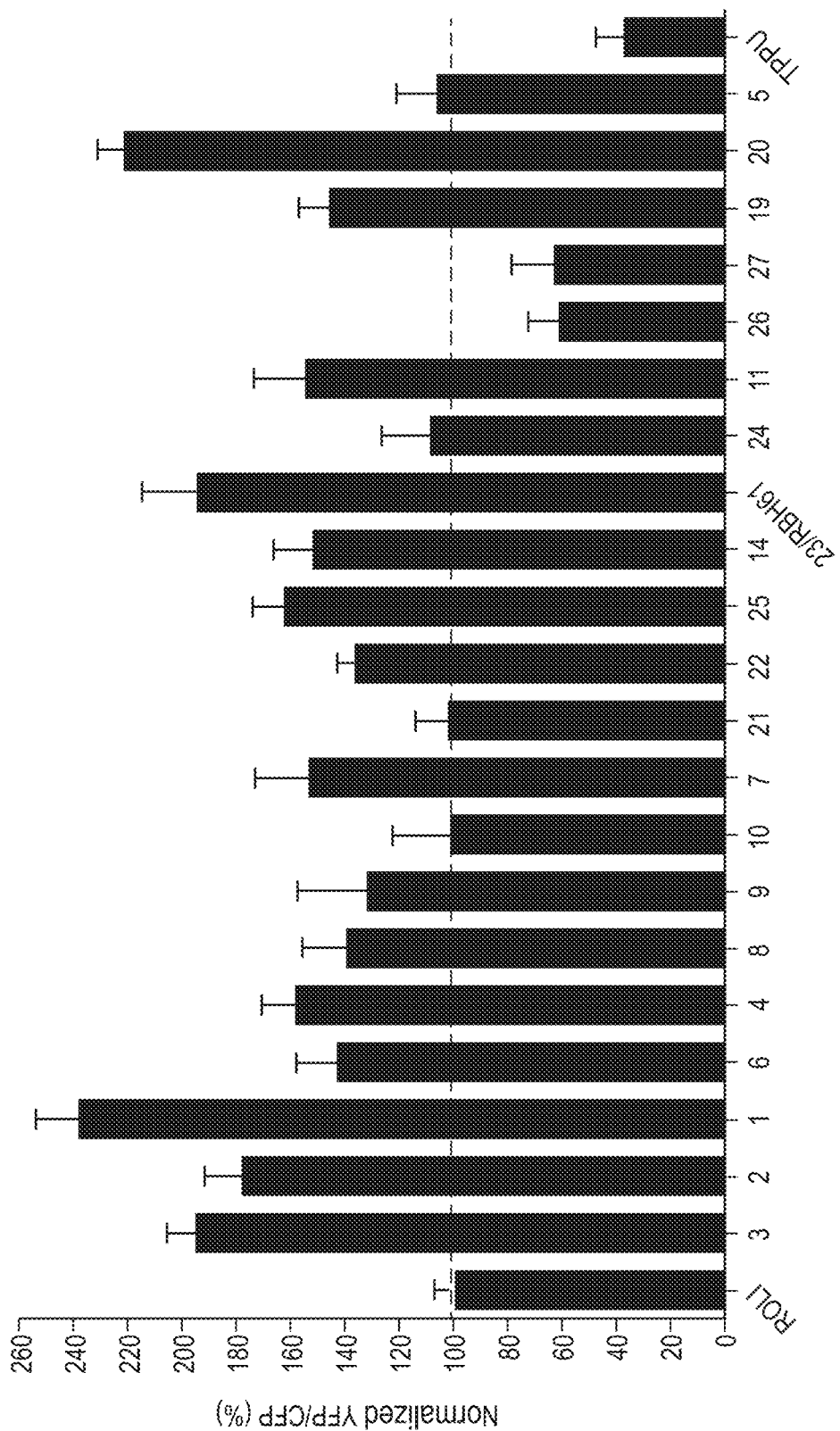
Figure 2C:
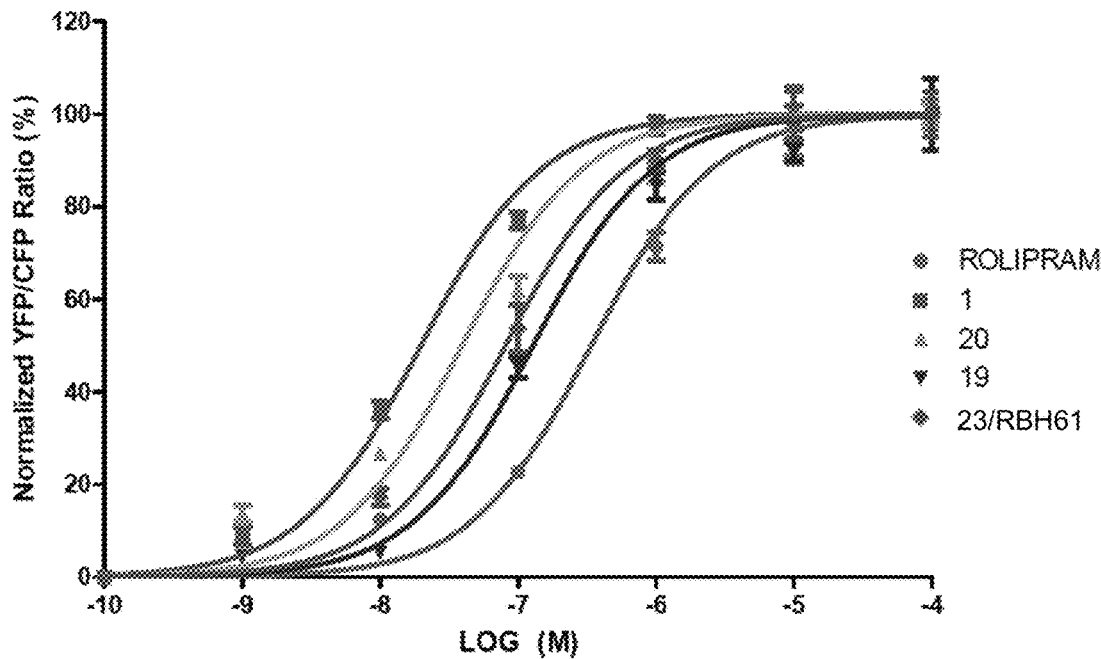

The normalized FRET ratio change values, percent change and number of cells of tested compounds and controls are summarized in Table 6. PKA activity triggered by novel compounds using FRET biosensor in HEK293 cells is shown in FIGS. 2A, 2B, and 2C.

TABLE 6

Normalized FRET ratio change values, percent change and number of cells

| ID | mean FRET ratio change | Percentage change | SD | Number of cells |
|---|---|---|---|---|
| Rolipram | 1.128 | 100 | 6.6 | 45 |
| 3 | 1.265 | 195 | 11.1 | 32 |
| 2 | 1.23 | 179 | 12.3 | 45 |
| 1 | 1.295 | 240 | 14.2 | 36 |
| 6 | 1.193 | 144 | 14.9 | 19 |
| 4 | 1.213 | 159 | 11.9 | 20 |
| 8 | 1.188 | 140 | 15.4 | 7 |
| 9 | 1.178 | 133 | 24.6 | 7 |
| 10 | 1.137 | 102 | 19.2 | 8 |
| 7 | 1.207 | 154 | 18.3 | 6 |
| 21 | 1.136 | 101 | 11.9 | 6 |
| 22 | 1.185 | 138 | 4.8 | 6 |
| 25 | 1.219 | 163 | 10.5 | 29 |
| 14 | 1.205 | 152 | 13.9 | 22 |
| 23/RBH61 | 1.263 | 195 | 19.1 | 11 |
| 24 | 1.147 | 110 | 16.5 | 7 |
| 11 | 1.209 | 156 | 17.3 | 8 |
| 26 | 1.083 | 62 | 10.2 | 9 |
| 27 | 1.085 | 63 | 14.1 | 6 |
| 19 | 1.218 | 147 | 9.3 | 18 |
| 20 | 1.276 | 223 | 8.7 | 14 |
| 5 | 1.155 | 107 | 13.1 | 9 |
| TPPU | 1.015 | 37 | 9.6 | 17 |

The in vitro screening process shown in tables 3-5, delivered 4 compounds with adequate potency on both targets and water solubility. To better characterize those 4 compounds melting points and additional $IC_{50}$ values were measured and compared to the single target model ligands (TPPU and Rolipram). Previous studies have shown a species dependent inhibition from human to murine she [Ref. 23]. As further in vivo evaluations are performed in a rat model, murine sEH $IC_{50}$ values were determined.

TABLE 7

Additional evaluation of four selected dual inhibitors $IC_{50}$ values and melting points

| ID | $IC_{50}(hsEH)^1$ [nM] | $IC_{50}(rsEH)^1$ [nM] | $IC_{50}(PDE4)^2$ [nM] | Melting point$^3$ (° C.) |
|---|---|---|---|---|
| TPPU$^4$ | 3.7 | 2.8 | — | 226 |
| Rolipram | — | — | 340 ± 0.06 | 127 |
| 1 | 0.6 ± 0.1 | 14 ± 1 | 1.9 ± 0.03 | 144 |
| 19 | 0.4 ± 0.1 | 1.3 ± 0.2 | 128 ± 0.05 | 106 |
| 20 | 0.4 ± 0 | 1.7 ± 0.2 | 3.9 ± 0.06 | 99 |
| 23/RBH61 | 2.1 ± 0.5 | 150 ± 16 | 8.1 ± 0.05 | 133 |
| 28 | 1.4 ± 0.1 | — | 9.3 ± 0.03 | — |

$^1$The sEH IC$_{50}$ values are recorded on recombinant human sEH protein (hsEH) and recombinant rat sEH protein (rsEH);
$^2$PDE4 inhibition was evaluated on cAMP increase in live HEK cells, transfected with a PKA biosensor;
$^3$Melting points were measured on an automated melting point system from Stanford Research Systems (OptiMelt-MPA100);
$^4$Literature values [Ref. 23].

Table 7 shows a drop in potency for compound 1, 19 and 20 by 2-3 fold. The potency of 23/RBH61 dropped by 75-fold compared to the human sEH inhibition. This drastic change in potency has not been documented for the sEH model ligand TPPU [Ref. 23]. Based on literature, PDE4 inhibition does not vary in-between human and rat according to the high structural similarity in the protein [Ref. 24 and Ref. 25].

Example 13: In Vivo Pharmacokinetic (PK) Evaluation

To identify one candidate for in vivo pain model, bioavailability of four dual compounds is determined in an in vivo pharmacokinetic cassette. 0.3 mg/kg of compound 1, 19, 20 and 23/RBH61 is administered per oral (PO) in four rats. Compound 1 is only detected at 0.5 h with a 3±2.2 nM plasma concentration, while compound 20 is not detected in the plasma. Compound 19 reaches a one digit nM plasma concentration and remains at that level for 12 h. Compound 23/RBH61 reaches the highest plasma concentration of 60±13 nM and is cleared after 4 h. Thus, 23/RBH61 has the best bioavailability of the in vivo cassette compounds (1, 19, 20 and 23/RBH61) and therefore qualifies for further in vivo evaluations. See Table 8 for details.

TABLE 8

In vivo plasma concentration of 3 compounds given as a cassette

| | ID | | |
|---|---|---|---|
| | 1 | 19 | 23/MPPA |
| Time (h) | Average (n = 4) plasma concentration (nM) | | |
| 0 | 0 | 0 | 0 |
| 0.25 | 0 | 2 ± 0.4 | 40 ± 10 |
| 0.5 | 3 ± 2.2 | 4 ± 1.3 | 60 ± 13 |
| 1 | 0 | 2 ± 0.3 | 40 ± 12 |
| 2 | 0 | 2 ± 0.3 | 25 ± 6 |
| 4 | 0 | 2 ± 0.2 | 2 ± 1.8 |
| 8 | 0 | 1 ± 0.1 | 0 |
| 12 | 0 | 1 ± 0.2 | 0 |
| 24 | 0 | 0.3 ± 0.01 | 0 |
| 48 | 0 | 0 | 0 |

Nevertheless, the plasma concentration achieved with 0.3 mg/kg PO application of 23/RBH61 is insufficient for sEH inhibition in a murine model, according to the rat sEH $IC_{50}$ value shown in Tables 3-5. Therefore, another PK study with increased doses of 23/RBH61 is indispensable.

3 mg/kg dose of 23/RBH61 results in 460±16 nM plasma concentration at 0.5 h and remains in the blood until 4 h. With the given dose of 3 mg/kg, plasma concentration is above the murine sEH $IC_{50}$ by a 3-fold and stays above the inhibitory concentration for almost 2 h. This PK study reveals that a 3 mg/kg dose of 23/RBH61 generates a therapeutic window of 2 h, which is sufficient for evaluation in murine model. Single experiments with doses of 30 mg/kg and 100 mg/kg resulted also in maximum concentrations at 0.5 h (1060 nM and 1730 nM). See Table 7 for details.

TABLE 7

In vivo PK study of 23/MPPA. Average plasma concentration values at 3 mg/kg oral dose in rats. Single measurments at 30 and 100 mg/kg

| | Dose | | |
|---|---|---|---|
| | 3 mg/kg (n = 4) | 30 mg/kg (n = 1) | 100 mg/kg (n = 1) |
| Time (h) | Plasma concentrations [nM] | | |
| 0 | 0 | 0 | 0 |
| 0.5 | 460 ± 16 | 1062 | 1733 |
| 1 | 400 ± 15 | 805 | 1383 |
| 2 | 120 ± 7 | 527 | 923 |
| 4 | 0 | 149 | 477 |
| 8 | 0 | 29 | 254 |
| 12 | 0 | 0 | 0 |
| 24 | 0 | 0 | 0 |
| 48 | 0 | 0 | 0 |

Thus, 23/RBH61 enriches rapidly in the plasma after oral application at different doses and has therefore potential as rapidly acting pharmaceutical agent, if a correlation to a pharmacodynamic effect can be established.

Example 14: Pharmacodynamic (PD) Evaluation In Vivo

Figure 3:
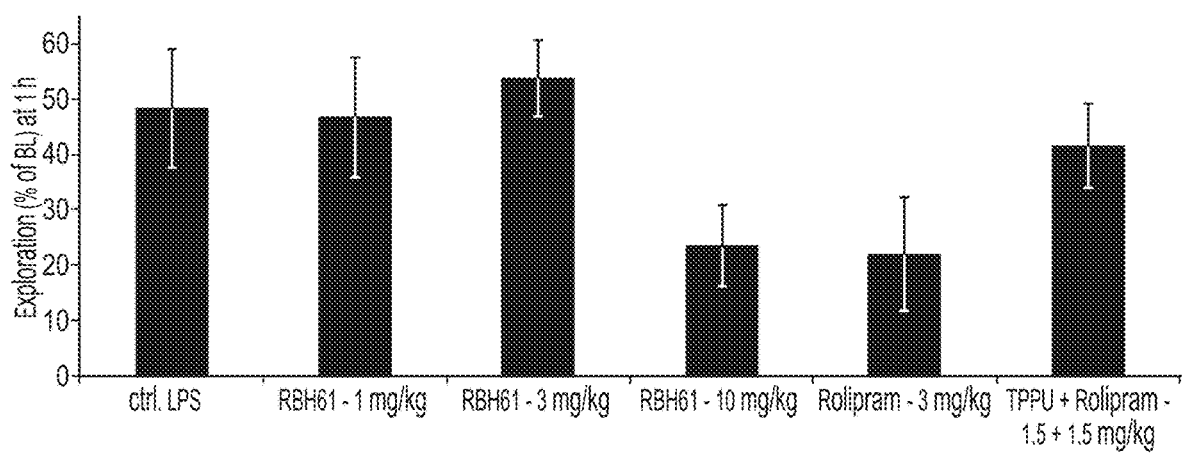
FIG. 3 shows the evaluation of exploration behavior. Exploration in percent of baseline (% of Bl.): 1 h after LPS injection and application of vehicle (PEG300), RBH61 at 1, 3 or 10 mg/kg, Rolipram at 3 mg/kg or a combination of TPPU and Rolipram at each 1.5 mg/kg. 100% represents the naïve animal behavior. Results are expressed in mean±SD. n=6 animals/group.

The evaluation of exploration behavior, shown in FIG. 3, provides information about the animal motor-skill condition under the influence of a given drug. The experiment reveals a first impression of the drug compatibility and the animals' capability of performing the thermal withdrawal threshold experiment.

As shown in FIG. 3, 1 h after injection of LPS in the right back paw and application of vehicle (PEG300) we document 50±11% remaining exploration compared to baseline. Following the application of RBH61 at 1 or 3 mg/kg exploration remains similar to the control group. The exploration declines after dosing RBH61 at 10 mg/kg or Rolipram at 3 mg/kg. The combination treatment of TPPU+Rolipram at each 1.5 mg/kg slightly decreases exploration.

Figure 4A:
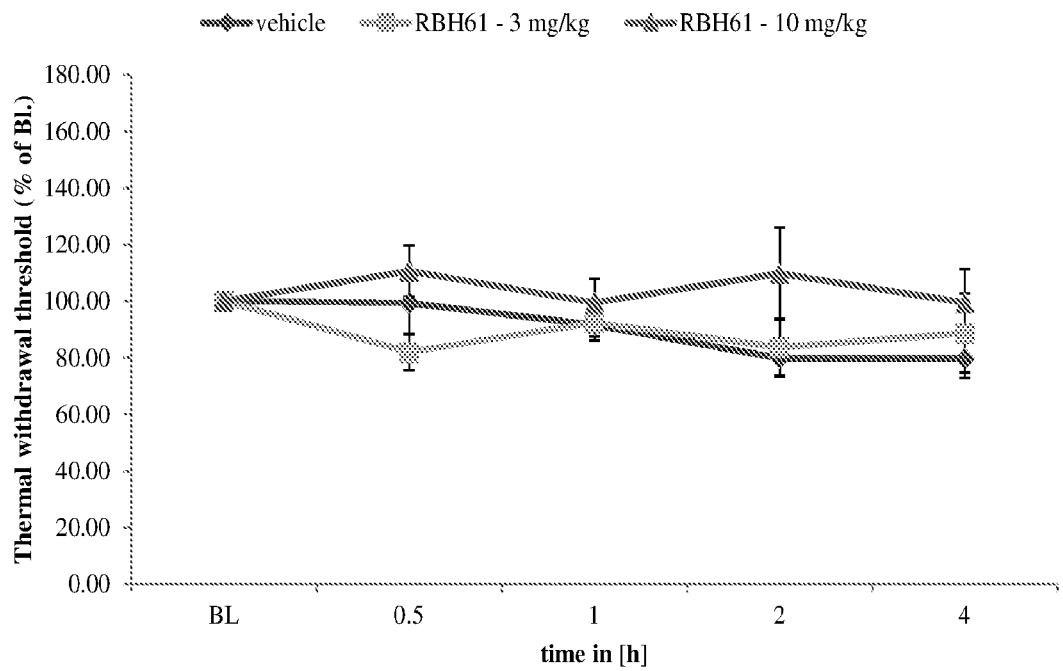
FIG. 4A shows the time course of TWL threshold in percent of baseline (% of Bl.) in naïve animals after application of vehicle (PEG300), RBH61 at 3 and 10 mg/kg over 4 h.
Figure 4B:
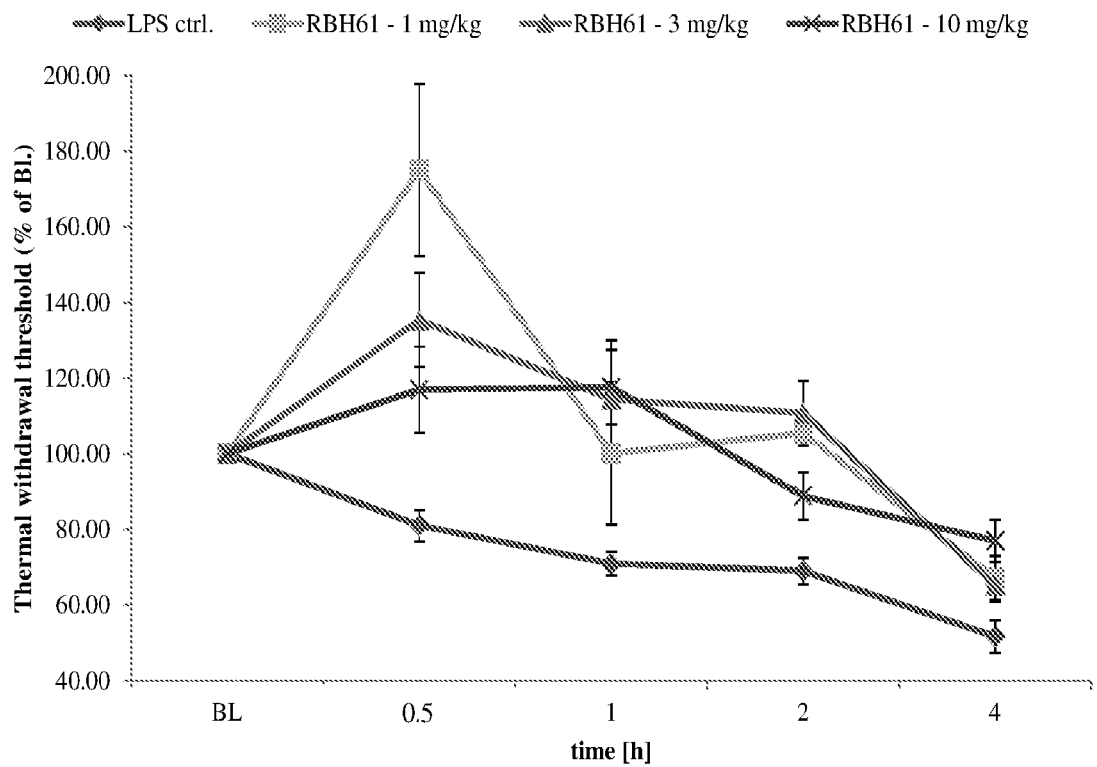
FIG. 4B shows the time course of TWL threshold in percent of baseline (% of Bl.) after LPS injection and application of vehicle (PEG300) or RBH61 at 1, 3 or 10 mg/kg over 4 h. 100% represents the naïve animal behavior. Results are expressed in mean±SD. n=6 animals/group.
Figure 5A:
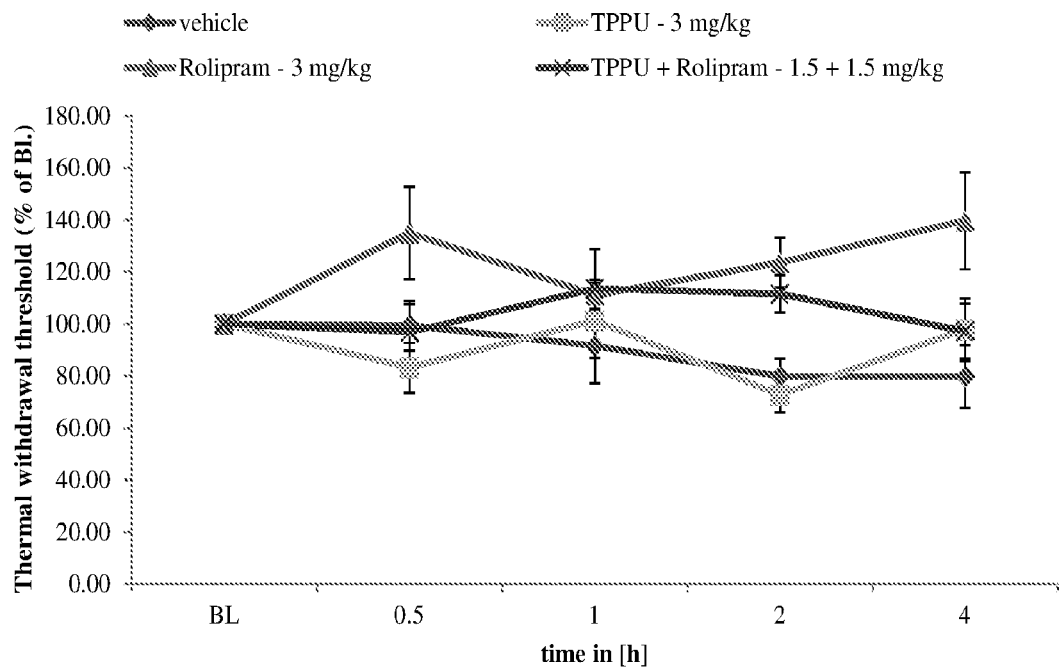
FIG. 5A shows the time course of TWL threshold in percent of baseline (% of Bl.) in naïve animals after application of vehicle (PEG300), TPPU and Rolipram at 3 mg/kg and a combination of both at each 1.5 mg/kg over 4 h.
Figure 5B:
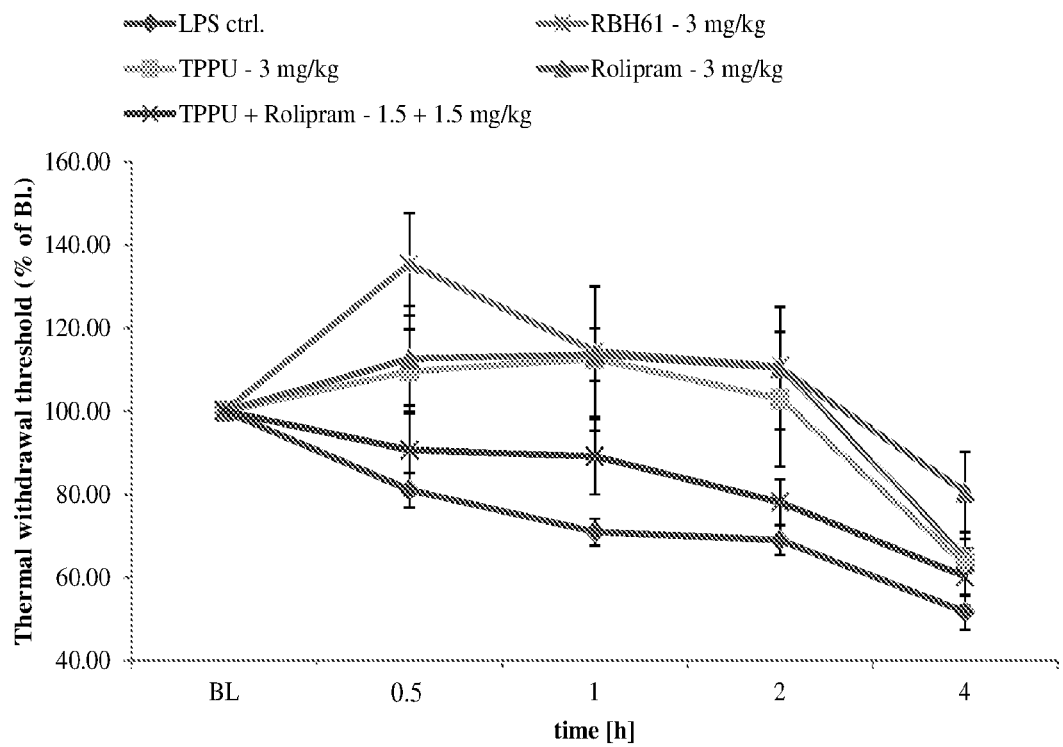
FIG. 5B shows the time course of TWL threshold in percent of baseline (% of Bl.) after LPS injection and application of vehicle (PEG300), RBH61, TPPU or Rolipram at 3 mg/kg or a combination of TPPU and Rolipram at each 1.5 mg/kg over 4 h. 100% represents the naïve animal behavior. Results are expressed in mean±SD. n=6 animals/group.

FIGS. 4B and 5B show the 4 h time course of the thermal withdrawal threshold (TWL) experiment. The TWL of naïve animals is determined before the experiment (see FIGS. 4A and 5A), followed by the induction of inflammatory pain in one back paw through an injection of lipopolysaccharide (LPS). FIG. 4B illustrates the TWL values in the LPS model after different doses of RBH61 (1, 3 or 10 mg/kg) compared to the vehicle group. Application of 1 or 3 mg/kg RBH61 results in a pain relief, reaching its peak at 0.5 h, which correlates with RBH61 $T_{max}$ plasma concentration. At a dose of 10 mg/kg RBH61 the analgesic effect in the TWL-LPS rat model declines.

FIG. 5B compares the dual target inhibitor RBH61 at a dose of 3 mg/kg in the TWL-LPS model with single target inhibitor TPPU and Rolipram each at a dose of 3 mg/kg and with a combination of both resulting in a total dose of 3 mg/kg (TPPU 1.5 mg/kg+Rolipram 1.5 mg/kg). The combination treatment (TPPU 1.5 mg/kg+Rolipram 1.5 mg/kg) achieves only a slight relief of inflammatory pain. Even with an increased combination dose (TPPU 3 mg/kg+Rolipram 3 mg/kg), shown in FIGS. 7A and 7B, the effect remains minor and notably below the effect generated by RBH61 at a 3 mg/kg dose.

Figure 6:
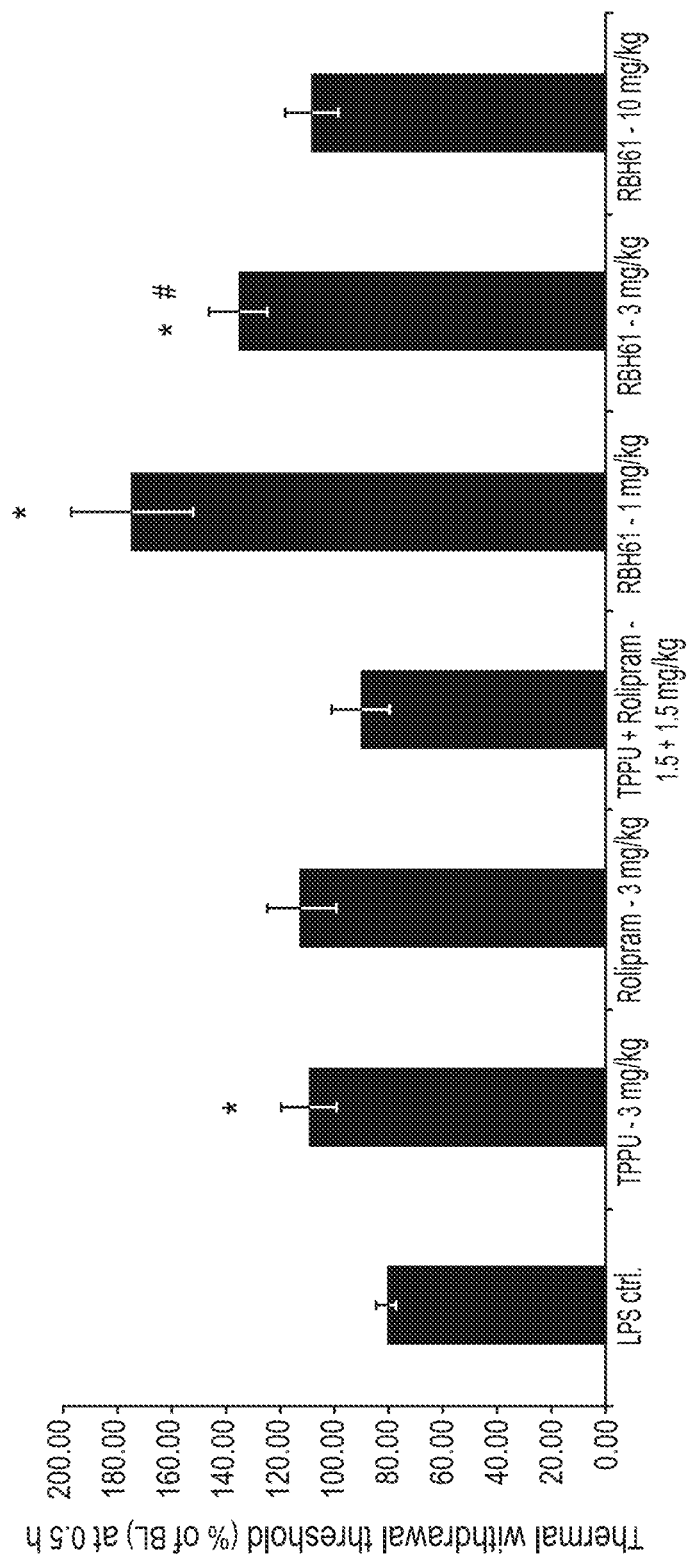
FIG. 6 shows the thermal withdrawal (TWL) threshold in percent of baseline (% of Bl.) at 0.5 h after LPS injection and application of vehicle (PEG300), RBH61 at 1, 3 or 10 mg/kg, TPPU or Rolipram at 3 mg/kg or a combination of TPPU and Rolipram at each 1.5 mg/kg. 100% represents the naïve animal behavior. Results are expressed in mean±SEM. n=6 animals/group. Student t-test was performed in excel to proof statistical significance (*$P<0.05$ compared to LPS control; #$P<0.05$ compared to reference treatments).

The previous performed PK study reveals a fast increase of RBH61 within 0.5 h in the plasma after oral application. FIG. 6 visualizes the analgesic effect of RBH61 at 0.5 h under inflammatory conditions, compared to reference treatments and their combinations.

Figure 7A:
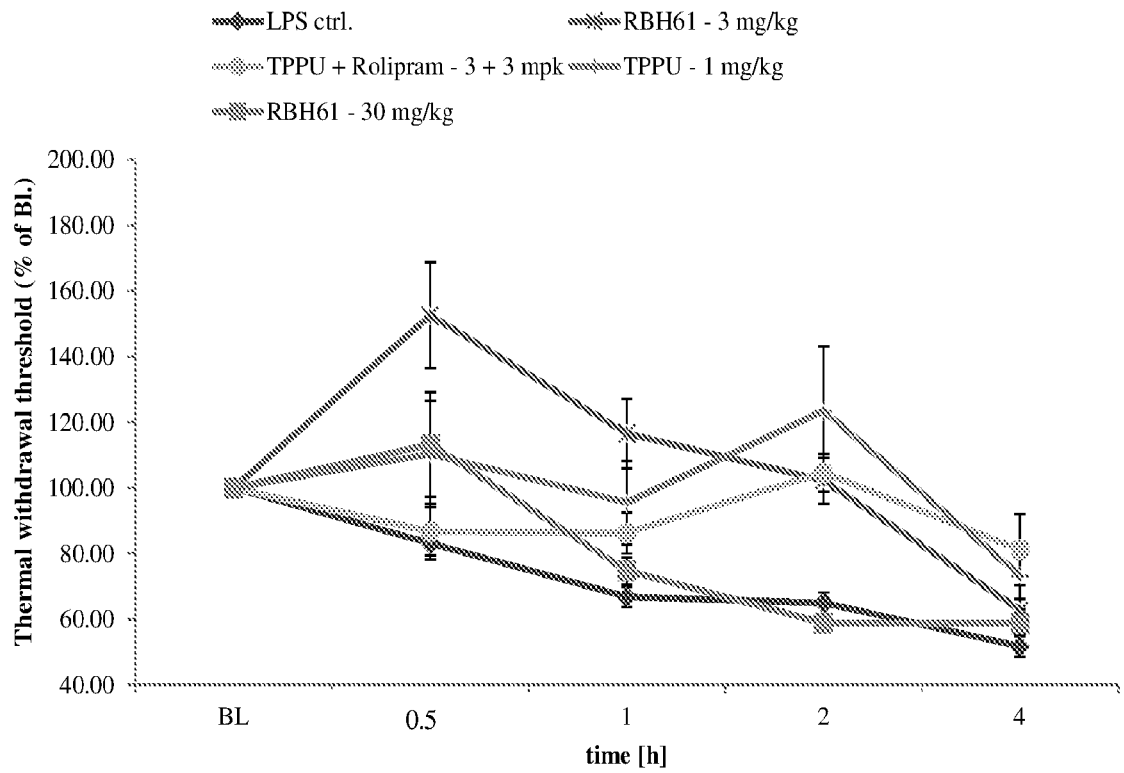
FIG. 7A shows the time course of thermal withdrawal (TWL) threshold in percent of baseline (% of Bl.) after LPS injection and application of vehicle (PEG300), RBH61 at 3 and 30 mg/kg, TPPU at 1 mg/kg and a combination of TPPU and Rolipram at each 3 mg/kg over 4 h.
Figure 7B:
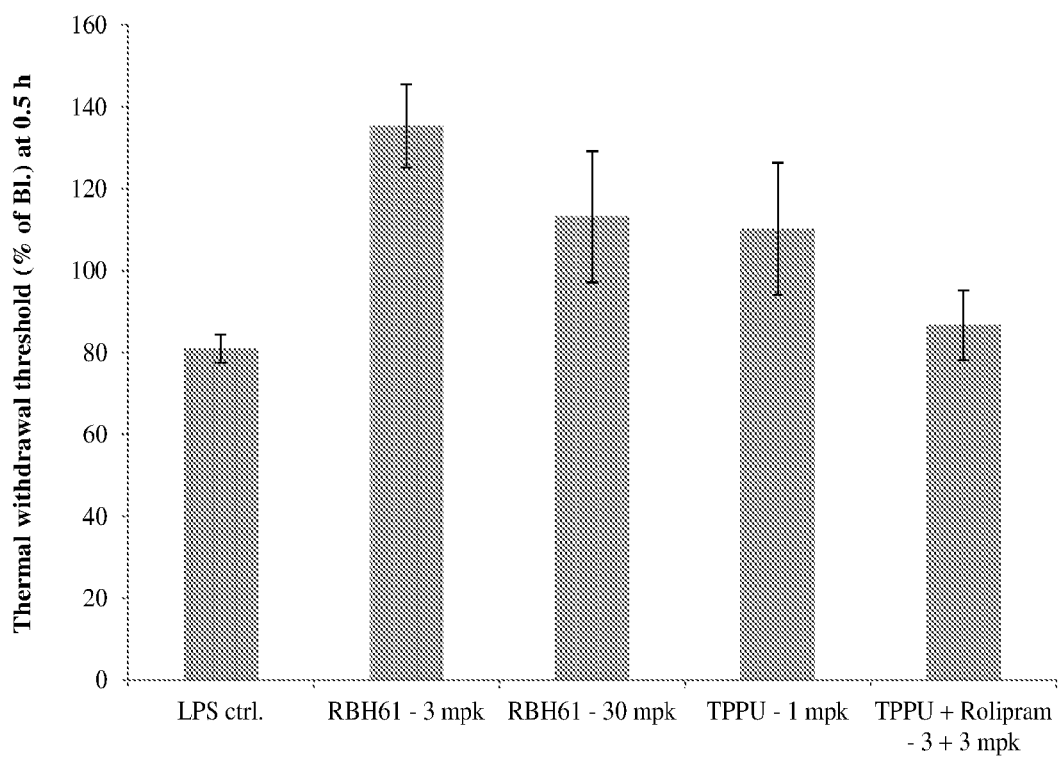
FIG. 7B shows the TWL threshold in percent of baseline (% of Bl.) at 0.5 h after LPS injection and application of vehicle (PEG300), RBH61 at 3 and 30 mg/kg, TPPU at 1 mg/kg and a combination of TPPU and Rolipram at each 3 mg/kg. 100% represents the naïve animal behavior. Results are expressed in mean±SD. n=3-6 animals/group.

At 0.5 h after induction of inflammatory pain, only RBH61 treated animals at a dose of 1 or 3 mg/kg, or TPPU treated animals at a dose of 3 mg/kg show a significant pain relief compared to the control LPS group (FIG. 6). The analgesic effect of RBH61 at 3 mg/kg at 0.5 h is also significantly higher than the single target treatments (TPPU—3 mg/kg or Rolipram—3 mg/kg, FIG. 6) and the combination of single target treatments (TPPU—1.5 mg/kg+Rolipram 1.5 mg/kg, FIG. 6). Additional experiments, presented in FIGS. 4B and 4C, show that a lower dose of TPPU (1 mg/kg) or a higher combination dose (TPPU—3 mg/kg+Rolipram—3 mg/kg) do not result in an equal analgesic effect compared to RBH61 at a 3 mg/kg dose at 0.5 h in the TWL-LPS model (FIGS. 7A and 7B).

Example 15: Discussion and Conclusion

This study was motivated by our previous research on synergism between sEH and PDE4 inhibitors [Ref. 1]. The previous study revealed a strong synergism on analgesia in naïve animals at different combinatorial doses of the sEH inhibitor TPAU and the PDE4 inhibitor Rolipram. Here, in the inflammatory pain model, we do not recognize any synergism caused by joint application of an even more potent sEH inhibitor (TPPU) and the same PDE4 inhibitor (Rolipram).

Nevertheless, this study delivered a bioavailable sEH/PDE4 dual inhibitor (RBH61) with a $T_{max}$ of 30 min and a simultaneously rapid analgesic onset under inflammatory conditions. The compound is cleared from the blood after 4 h at a dose of 3 mg/kg, which now gives the opportunity to further evaluate the sEH/PDE4 dual approach in vivo.

Increased doses of RBH61, such as 10 mg/kg, do not further enhance the analgesic effect, due to casualties which still have to be discovered. An increase in urine excretion is observable over the following days post RBH61 treatment. The diuretic effect could be involved in the efficacy loss at high doses of RBH61. Doses lower 1 mg/kg of RBH61 cannot be evaluated in murine models, due to the lack of species dependent target engagement. Though, in human the 75-fold higher potency towards sEH would allow several lower doses of RBH61 to be evaluated.

In this study 21 novel sEH/PDE4 dual inhibitors are designed, synthesized and their high potency on both targets is established in vitro. Through pharmacokinetic evaluations one dual inhibitor (RBH61) was characterized as sufficient for in vivo studies. RBH61, therefore, represents a new tool compound supporting research in medicinal chemistry. RBH61 rapidly increases in the plasma after oral application ($T_{max}$=0.5 h) and reduces inflammatory pain at the same high rate, demonstrated in a rat TWL-LPS model.

The analgesic effect on inflammatory pain 30 min post treatment is significantly higher with RBH61 at 3 mg/kg, compared to the single target treatment with TPPU, Rolipram or their combination at equivalent doses. Surprisingly no synergism is observed between sEH inhibitor TPPU and PDE4 inhibitor Rolipram at different doses in the TWL-LPS rat model. Control groups of naïve rats treated with RBH61 show no analgesic effect.

RBH61 at a dose of 1 or 3 mg/kg does not affect the animal motor skills in the inflammatory diseased state, while Rolipram or a combination of Rolipram and TPPU at a total dose of 3 mg/kg diminishes the animal exploration behaviour. This indicates that at a total dose of 3 mg/kg RBH61 has a better compatibility than Rolipram or the combination of TPPU and Rolipram in a rat LPS model. But with high doses of RBH61 (10 mg/kg) exploration decrease appears; conform to the efficacy decline in the rat LPS model.

The PK/PD data produced in this study initiates the characterization of RBH61. The data reveals a novel compound with a fast appearance in the plasma after oral application, which translates into a rapid relief of inflammatory pain. Further evaluations of this novel sEH/PDE4 dual compound will have to be performed to clarify its pharmacological value. Based on the target engagement of RBH61, more disease indications are worth exploring, for example depression and COPD.

VI. References (1) Inceoglu, B.; Wagner, K.; Schebb, N. H.; Morisseau, C.; Jinks, S. L.; Ulu, a.; Hegedus, C.; Rose, T.; Brosnan, R.; Hammock, B. D. Analgesia Mediated by Soluble Epoxide Hydrolase Inhibitors Is Dependent on cAMP. *Proc. Nat. Acad. Sci.* 2011, 108 (12), 5093-5097.

(2) Reddy, A. S.; Zhang, S. Polypharmacology: Drug Discovery for the Future. *Expert Rev. Clin. Pharmacol.* 2013, 6 (1), 41-47.

(3) Blöcher, R.; Lamers, C.; Wittmann, S. K.; Merk, D.; Hartmann, M.; Weizel, L.; Diehl, O.; Brüggerhoff, A.; Boß, M.; Kaiser, A.; Schader, T.; Göbel, T.; Grundmann, M.; Angioni, C.; Heering, J.; Geisslinger, G.; Wurglics, M.; Kostenis, E.; Brune, B.; Steinhilber, D.; Schubert-Zsilavecz, M.; Kahnt, A. S.; Proschak, E. N-Benzylbenzamides: A Novel Merged Scaffold for Orally Available Dual Soluble Epoxide Hydrolase/Peroxisome Proliferator-Activated Receptor Gamma Modulators. *J. Med. Chem.* 2016, 59 (1), 61-81.

(4) la Buscató, E.; Blöcher, R.; Lamers, C.; Klingler, F.-M.; Hahn, S.; Steinhilber, D.; Schubert-Zsilavecz, M.; Proschak, E. Design and Synthesis of Dual Modulators of Soluble Epoxide Hydrolase and Peroxisome Proliferator-Activated Receptors. *J. Med. Chem.* 2012, 55, 10771-10775.

(5) Meirer, K.; Glatzel, D.; Kretschmer, S.; Wittmann, S.; Hartmann, M.; Blöcher, R.; Angioni, C.; Geisslinger, G.; Steinhilber, D.; Hofmann, B.; Fürst, R.; Proschak, E. Design, Synthesis and Cellular Characterization of a Dual Inhibitor of 5-Lipoxygenase and Soluble Epoxide Hydrolase. *Molecules* 2016, 22 (1), 45.

(6) Morisseau, C.; Hammock, B. D. Impact of Soluble Epoxide Hydrolase and Epoxyeicosanoids on Human Health. *Annu. Rev. Pharmacol. Toxicol.* 2013, 53, 37-58.

(7) Mclellan, G. J.; Aktas, Z.; Hennes-beean, E.; Kolb, A. W.; Larsen, V.; Schmitz, E. J.; Clausius, H. R.; Yang, J.; Hwang, S. H.; Morisseau, C.; Inceoglu, B.; Hammock, B. D.; Brandt, C. R. Induced Uveitis in the Rabbit. *J Ocul. Biol.* 2017, 4 (1), 1-17.

(8) Wagner, K.; Inceoglu, B.; Hammock, B. D. Soluble Epoxide Hydrolase Inhibition, Epoxygenated Fatty Acids and Nociception. *Prostaglandins Other Lipid Mediat.* 2011, 96 (1-4), 76-83.

(9) Ren, Q.; Ma, M.; Ishima, T.; Morisseau, C.; Yang, J.; Wagner, K. M.; Zhang, J. Gene Deficiency and Pharmacological Inhibition of Soluble Epoxide Hydrolase Confers Resilience to Repeated Social Defeat Stress. *Proc. Natl. Acad. Sci. U.S.A* 2016, 1-9.

(10) Perez-Aso, M.; Montesinos, M. C.; Mediero, A.; Wilder, T.; Schafer, P. H.; Cronstein, B. Apremilast, a Novel Phosphodiesterase 4 (PDE4) Inhibitor, Regulates Inflammation through Multiple cAMP Downstream Effectors. *Arthritis Res. Ther.* 2015, 17, 249.

(11) Brown, W. M. Treating COPD with PDE 4 Inhibitors. *Int. J COPD* 2007, 2 (4), 517-533.

(12) Ashton, M. J.; Cook, D. C.; Fenton, G.; Karlsson, J. A.; Palfreyman, M. N.; Raebum, D.; Ratcliffe, A. J.; Souness, J. E.; Thurairatnam, S.; Vicker, N. Selective Type IV Phosphodiesterase Inhibitors as Antiasthmatic Agents. The Syntheses and Biological Activities of 3-(Cyclopentyloxy)-4-Methoxybenzamides and Analogues. *J. Med. Chem.* 1994, 37(11), 1696-1703.

(13) Fujita, M.; Richards, E. M.; Niciu, M. J.; Hines, C. S.; Pike, V. W.; Jr, C. A. Z. cAMP Signaling in Brain Is Decreased in Unmedicated Depressed Patients and Increased by Treatment with a Selective Serotonin Reuptake Inhibitor. 2016, *Mol Psychi* (Article in press), 1-6.

(14) Brandon, N. J. Uncovering the Function of Disrupted in Schizophrenia 1 through Interactions with the cAMP Phosphodiesterase PDE4: Contributions of the Houslay Lab to Molecular Psychiatry. *Cell. Signal.* 2016, 28 (7), 749-752.

(15) Gurney, M. E.; D'Amato, E. C.; Burgin, A. B. Phosphodiesterase-4 (PDE4) Molecular Pharmacology and Alzheimer's Disease. *Neurotherapeutics* 2015, 12 (1), 49-56.

(16) Podolin, P. L.; Bolognese, B. J.; Foley, J. F.; Long, E.; Peck, B.; Umbrecht, S.; Zhang, X.; Zhu, P.; Schwartz, B.; Xie, W.; Quinn, C.; Qi, H.; Sweitzer, S.; Chen, S.; Galop, M.; Ding, Y.; Belyanskaya, S. L.; Israel, D. I.; Morgan, B. A.; Behm, D. J.; Marino, J. P.; Kurali, E.; Barnette, M. S.; Mayer, R. J.; Booth-Genthe, C. L.; Callahan, J. F. In Vitro and in Vivo Characterization of a Novel Soluble Epoxide Hydrolase Inhibitor. *Prostaglandins Other Lipid Mediat.* 2013, 104-105, 25-31.

(17) Lazaar, A. L.; Yang, L.; Boardley, R. L.; Goyal, N. S.; Robertson, J.; Baldwin, S. J.; Newby, D. E.; Wilkinson, I. B.; Tal-Singer, R.; Mayer, R. J.; Cheriyan, J. Pharmacokinetics, Pharmacodynamics and Adverse Event Profile of GSK2256294, a Novel Soluble Epoxide Hydrolase Inhibitor. *Br. J. Clin. Pharmacol.* 2016, 81 (5), 971-979.

(18) Card, G. L.; England, B. P.; Suzuki, Y.; Fong, D.; Powell, B.; Lee, B.; Luu, C.; Tabrizizad, M.; Gillette, S.; Ibrahim, P. N.; Artis, D. R.; Bollag, G.; Milburn, M. V.; Kim, S. H.; Schlessinger, J.; Zhang, K. Y. J. Structural Basis for the Activity of Drugs That Inhibit Phosphodiesterases. *Structure* 2004, 12 (12), 2233-2247.

(19) Lee, K. S. S.; Liu, J. Y.; Wagner, K. M.; Pakhomova, S.; Dong, H.; Morisseau, C.; Fu, S. H.; Yang, J.; Wang, P.; Ulu, A.; Mate, C. A.; Nguyen, L. V.; Hwang, S. H.; Edin, M. L.; Mara, A. A.; Wulff, H.; Newcomer, M. E.; Zeldin, D. C.; Hammock, B. D. Optimized Inhibitors of Soluble Epoxide Hydrolase Improve in Vitro Target Residence Time and in Vivo Efficacy. *J. Med. Chem.* 2014, 57 (16), 7016-7030.

(20) Brown, A.; Rawson, D.; Storer, R.; Swain, A. Patent (WO2012/007868 A2). 2012.

(21) Anandan, S. K.; Webb, H. K.; Chen, D.; Wang, Y. X.; Aavula, B. R.; Cases, S.; Cheng, Y.; Do, Z. N.; Mehra, U.; Tran, V.; Vincelette, J.; Waszczuk, J.; White, K.; Wong, K. R.; Zhang, L. N.; Jones, P. D.; Hammock, B. D.; Patel, D. V.; Whitcomb, R.; MacIntyre, D. E.; Sabry, J.; Gless, R. 1-(1-Acetyl-Piperidin-4-Yl)-3-Adamantan-1-Yl-Urea (AR9281) as a Potent, Selective, and Orally Available Soluble Epoxide Hydrolase Inhibitor with Efficacy in Rodent Models of Hypertension and Dysglycemia. *Bioorganic Med. Chem. Lett.* 2011, 21 (3), 983-988.

(22) Zhao, Z.; Pissamitski, D. A.; Josien, H. B.; Bara, T. A.; Clader, J. W.; Li, H.; McBriar, M. D.; Rajagopalan, M.; Xu, R.; *Terracina*, G.; Hyde, L.; Song, L.; Zhang, L.; Parker, E. M.; Osterman, R.; Buevich, A. V. Substituted 4-Morpholine N-Arylsulfonamides as Gamma-Secretase Inhibitors. *Eur. J. Med. Chem.* 2016, 124, 36-48.

(23) Rose, T. E.; Morisseau, C.; Liu, J. Y.; Inceoglu, B.; Jones, P. D.; Sanbom, J. R.; Hammock, B. D. 1-Aryl-3-(1-Acylpiperidin-4-Yl)urea Inhibitors of Human and Murine Soluble Epoxide Hydrolase: Structure-Activity Relationships, Pharmacokinetics, and Reduction of Inflammatory Pain. *J. Med. Chem.* 2010, 53 (19), 7067-7075.

(24) Soto, D.; De Arcangelis, V.; Zhang, J.; Xiang, Y. K.; Liu, S.; Li, Y.; Kim, S.; Fu, Q.; Parikh, D.; Sridhar, B.; Shi, Q.; Zhang, X.; Guan, Y.; Chen, X.; Xiang, Y. K. Phosphodiesterases Coordinate cAMP Propagation Induced by Two Stimulatory G Protein-Coupled Receptors in Hearts. *Circ. Res.* 2009, 109 (17), 6578-6583.

(25) Richter, W.; Xie, M.; Scheitrum, C.; Krall, J.; Movsesian, M. A.; Conti, M.; Bian, H.; Zhang, J.; Wu, P.; Varty, L. A.; Jia, Y.; Mayhood, T.; Hey, J. A.; Wang, P. Differential Type 4 cAMP-Specific Phosphodiesterase (PDE4) Expression and Functional Sensitivity to PDE4 Inhibitors among Rats, Monkeys and Humans. *Basic Res. Cardiol.* 2011, 106 (11), 249-262.

(26) Jones, P. D.; Wolf, N. M.; Morisseau, C.; Whetstone, P.; Hock, B.; Hammock, B. D. Fluorescent Substrates for Soluble Epoxide Hydrolase and Application to Inhibition Studies. *Anal. Biochem.* 2005, 343 (1), 66-75.

(27) Liu, J. Y.; Lin, Y. P.; Qiu, H.; Morisseau, C.; Rose, T. E.; Hwang, S. H.; Chiamvimonvat, N.; Hammock, B. D. Substituted Phenyl Groups Improve the Pharmacokinetic Profile and Anti-Inflammatory Effect of Urea-Based Soluble Epoxide Hydrolase Inhibitors in Murine Models. *Eur. J Pharm. Sci.* 2013, 48 (4-5), 619-627.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of formula I:

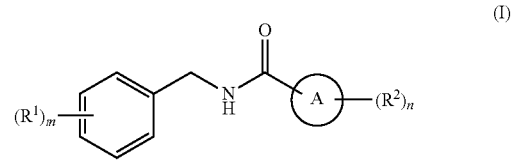

or a pharmaceutically acceptable salt thereof, wherein:

each $R^1$ is independently halogen, $C_1$-$C_6$ alkyl, $C_1$-$C_6$ haloalkyl, $C_1$-$C_6$ alkoxy, or $C_1$-$C_6$ haloalkoxy;

ring A is 3 to 8 membered heterocycloalkyl, or $C_6$-$C_{12}$ aryl, wherein the 3 to 8 membered heterocycloalkyl has 1 to 4 heteroatoms of N, O, and S;

each $R^2$ is independently hydrogen, halogen, $C_1$-$C_6$ alkyl, $C_1$-$C_6$ haloalkyl, —C(O)NR$^3$R$^4$, —NR$^3$C(O)R$^5$, —C(O)OR$^5$, —OC(O)R$^5$, —C(O)R$^5$, —SO$_2$NR$^3$R$^4$, —NR$^3$SO$_2$R$^5$, —SO$_2$R$^5$, —NR$^3$R$^4$, or —OR$^5$;

$R^3$, $R^4$, and $R^5$ are each independently hydrogen, $C_1$-$C_6$ alkyl, $C_1$-$C_6$ haloalkyl, or $C_3$-$C_8$ cycloalkyl;

subscript m is an integer from 1 to 5; and subscript n is an integer from 1 to 4.

2. The compound of claim 1, wherein subscript m is an integer from 1 to 2.

3. The compound of claim 2, having formula I-1:

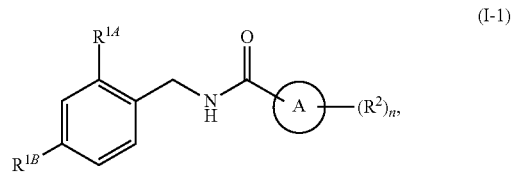

wherein:

$R^{1A}$ and $R^{1B}$ are independently hydrogen, halogen, $C_1$-$C_6$ alkyl, $C_1$-$C_6$ haloalkyl, $C_1$-$C_6$ alkoxy, or $C_1$-$C_6$ haloalkoxy, provided that $R^{1A}$ and $R^{1B}$ are not both hydrogen.

4. The compound of claim 3, wherein $R^{1A}$ is —CF$_3$.

5. The compound of claim 3, wherein $R^{1B}$ is —OCH$_3$.

6. The compound of claim 3, having formula 1-2:

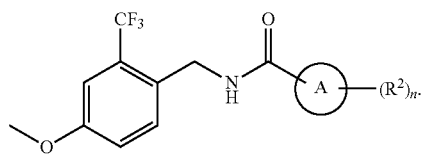

7. The compound of claim 1, wherein subscript n is an integer from 1 to 2.

8. The compound of claim 1, wherein ring A is phenyl.

9. The compound of claim 8, having formula 1-3:

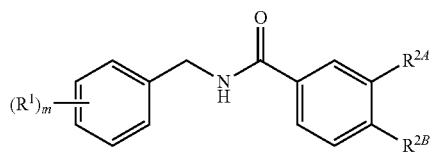

wherein:

$R^{2A}$ and $R^{2B}$ are each independently hydrogen, halogen, $C_1$-$C_6$ alkyl, $C_1$-$C_6$ haloalkyl, —C(O)NR$^3$R$^4$, —NR$^3$C(O)R$^5$, —C(O)OR$^5$, —OC(O)R$^5$, —C(O)R$^5$, —SO$_2$NR$^3$R$^4$, —NR$^3$SO$_2$R$^5$, —SO$_2$R$^5$, —NR$^3$R$^4$, or —OR$^5$; and $R^3$, $R^4$, and $R^5$ are each independently hydrogen, $C_1$-$C_6$ alkyl, $C_1$-$C_6$ haloalkyl, or $C_3$-$C_8$ cycloalkyl.

10. The compound of claim 8, having formula I-2a:

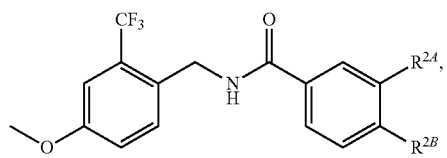

wherein:

$R^{2A}$ and $R^{2B}$ are each independently hydrogen, halogen, $C_1$-$C_6$ alkyl, $C_1$-$C_6$ haloalkyl, —NHC(O)R$^5$, or —OR$^5$; and $R^5$ is hydrogen, $C_1$-$C_6$ alkyl, $C_1$-$C_6$ haloalkyl, or $C_3$-$C_8$ cycloalkyl.

11. The compound of claim 10, wherein $R^{2A}$ is hydrogen, —NHC(O)—$C_1$-$C_6$ alkyl, or —O—$C_3$-$C_8$ cycloalkyl.

12. The compound of claim 11, wherein $R^{2A}$ is —O—$C_3$-$C_8$ cycloalkyl.

13. The compound of claim 10, wherein $R^{2B}$ is hydrogen, halogen, $C_1$-$C_6$ alkyl, —NHC(O)—$C_1$-$C_6$ alkyl, —O—$C_1$-$C_6$ alkyl, or —O—$C_1$-$C_6$ haloalkyl.

14. The compound of claim 9, selected from the group consisting of:

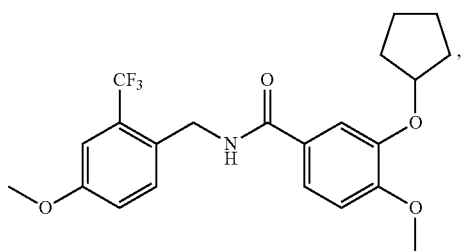

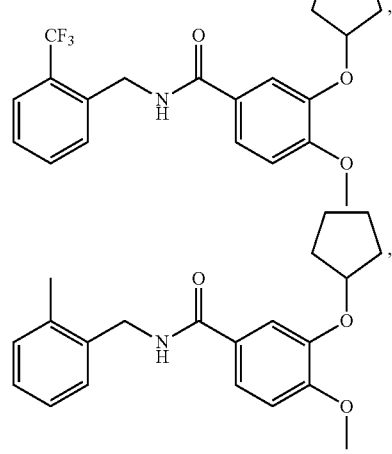

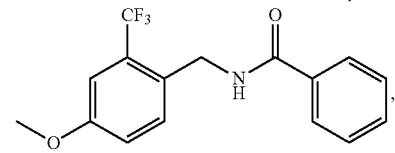

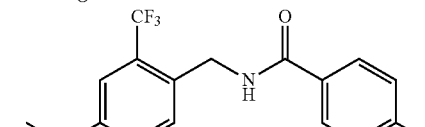

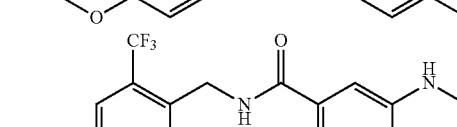

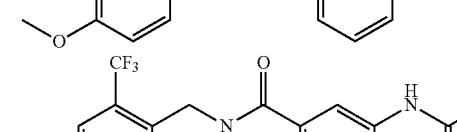

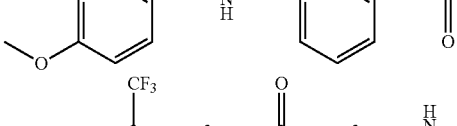

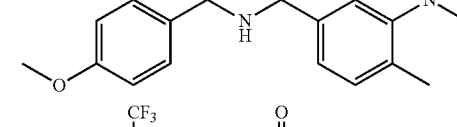

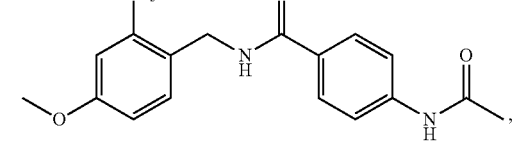

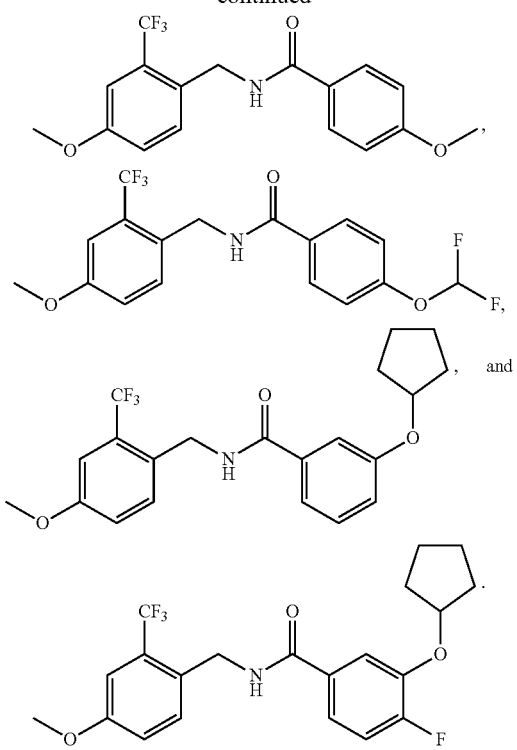

15. The compound of claim 10, selected from the group consisting of:

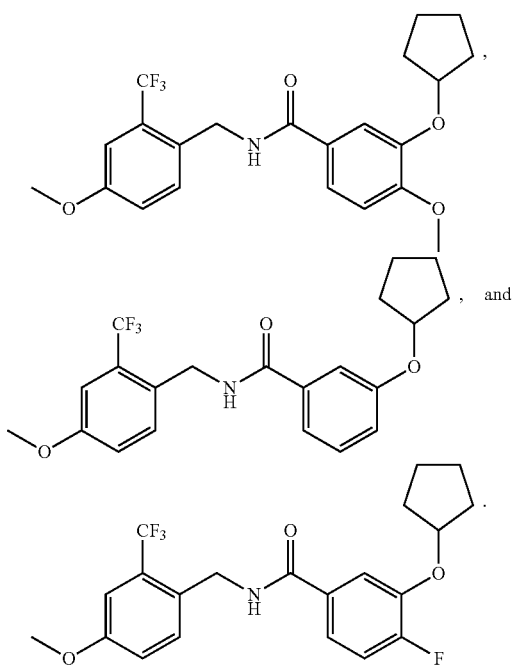

16. The compound of claim 1, wherein ring A is 3-8 membered heterocycloalkyl having at least one nitrogen atom.

17. The compound of claim 16, wherein ring A is piperidinyl.

18. The compound of claim 17, having formula 1-4:

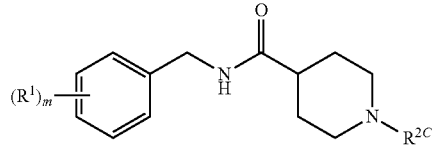

wherein:
R$^{2C}$ is hydrogen, C$_1$-C$_6$ alkyl, C$_1$-C$_6$ haloalkyl, —C(O)NR$^3$R$^4$, —C(O)OR$^5$, —C(O)R$^5$, —SO$_2$NR$^3$R$^4$, or —SO$_2$R$^5$; and
R$^3$, R$^4$, and R$^5$ are each independently hydrogen, C$_1$-C$_6$ alkyl, C$_1$-C$_6$ haloalkyl, or C$_3$-C$_8$ cycloalkyl.

19. The compound of claim 17, having formula I-2b:

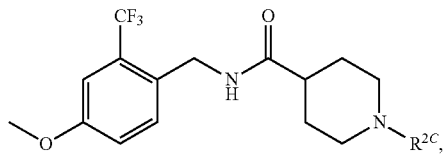

wherein:
R$^{2C}$ is hydrogen, C$_1$-C$_6$ alkyl, C$_1$-C$_6$ haloalkyl, —C(O)OR$^5$, or —C(O)R$^5$; and
R$^5$ is hydrogen, C$_1$-C$_6$ alkyl, C$_1$-C$_6$ haloalkyl, or C$_3$-C$_8$ cycloalkyl.

20. The compound of claim 19, wherein R$^{2C}$ is hydrogen, C$_1$-C$_6$ alkyl, —C(O)O—C$_1$-C$_6$ alkyl, —C(O)—C$_1$-C$_6$ alkyl, or —C(O)—C$_3$-C$_8$ cycloalkyl.

21. The compound of claim 19, selected from the group consisting of:

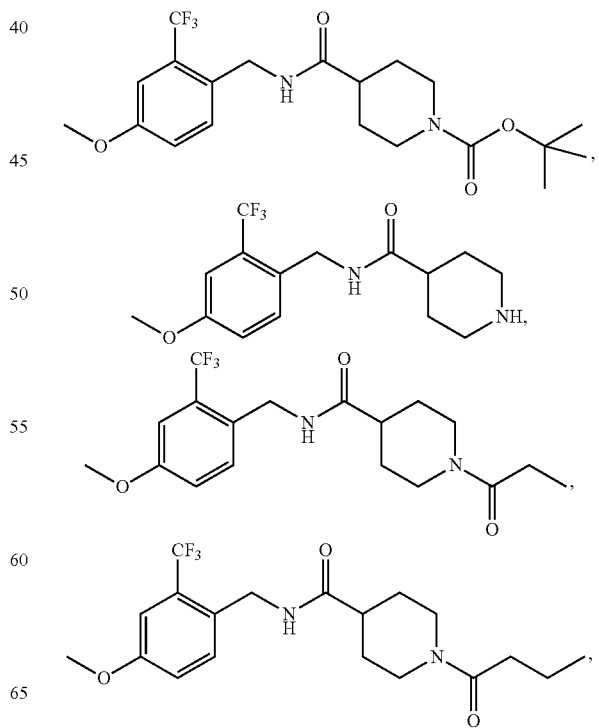

-continued

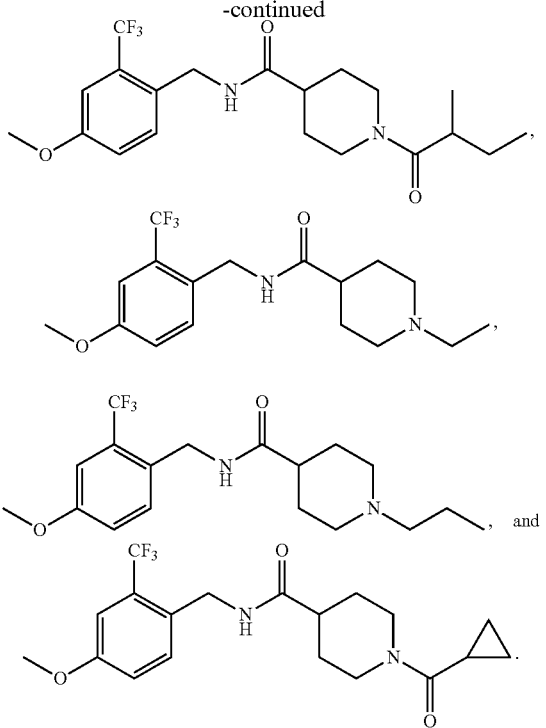

22. The compound of claim 19, having the formula:

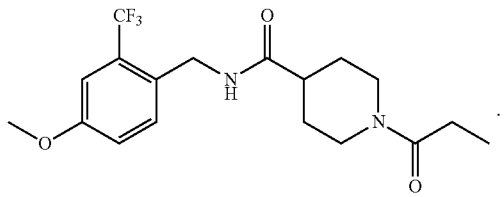 [SMILES: CCC(=O)N1CCC(C(=O)NCc2ccc(OC)cc2C(F)(F)F)CC1]

23. A pharmaceutical composition comprising the compound of claim 1 and one or more pharmaceutically acceptable excipient.

24. A method of inhibiting soluble epoxide hydrolase (sEH) and phosphodiesterase 4 (PDE4), the method comprising contacting the soluble epoxide hydrolase (sEH) and phosphodiesterase 4 (PDE4) with an effective amount of a compound of claim 1, or the pharmaceutical composition of claim 23.

25. A method of treating pain, said method comprising administering to a subject in need thereof a therapeutically effective amount of a compound of one of claim 1, or the pharmaceutical composition of claim 23.

* * * * *